(12) United States Patent
Tsimikas et al.

(10) Patent No.: US 9,347,959 B2
(45) Date of Patent: May 24, 2016

(54) OXIDATIVE BIOMARKERS IN PREDICTING RISK OF STROKE, TRANSIENT ISCHEMIC ATTACK (TIA) AND PERIPHERAL ARTERIAL DISEASE (PAD)

(71) Applicant: The Regents of the University of California, Oakland, CA (US)

(72) Inventors: Sotirios Tsimikas, San Diego, CA (US); Joseph L. Witztum, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/416,555

(22) PCT Filed: Jul. 24, 2013

(86) PCT No.: PCT/US2013/051839
§ 371 (c)(1),
(2) Date: Jan. 22, 2015

(87) PCT Pub. No.: WO2014/018643
PCT Pub. Date: Jan. 30, 2014

(65) Prior Publication Data
US 2015/0185239 A1    Jul. 2, 2015

Related U.S. Application Data

(60) Provisional application No. 61/675,164, filed on Jul. 24, 2012.

(51) Int. Cl.
*G01N 33/53* (2006.01)
*G01N 33/92* (2006.01)
*G01N 33/68* (2006.01)

(52) U.S. Cl.
CPC ............ *G01N 33/92* (2013.01); *G01N 33/6893* (2013.01); *G01N 2333/775* (2013.01); *G01N 2405/04* (2013.01); *G01N 2800/2871* (2013.01); *G01N 2800/50* (2013.01)

(58) Field of Classification Search
None
See application file for complete search history.

(56) References Cited

U.S. PATENT DOCUMENTS

| 7,939,287 B2 | 5/2011 | Tsimikas et al. |
| 2006/0177435 A1* | 8/2006 | Tsimikas et al. ........... 424/133.1 |
| 2012/0171705 A1 | 7/2012 | Mallat et al. |

OTHER PUBLICATIONS

Wells (1990) Biochemistry 29: 8509-8517.*
Ngo et al. (1995) "The Protein Folding Problem and Tertiary Structure Prediction, Chapter 14: Computational Complexity Protein Structure Prediction, and the Levinthal Paradox" from p. 434-506, particular at pp. 492-495 Editor by Merz et al.*
Bork (2000) Genome Research 10:398-400.*
Skolnick (2000) Trends in Biotech. 18: 34-39.*
Smith et al. (1997) Nature Biotechnology 1999 15: 1222-1223).*
Kiechl et al., "Oxidized phospholipids, lipoprotein(a), Lipoprotein-associated phospholipaase A2 activity, and 10-year cardiovascular outcomes prospective results from the bruneck Study,"Arteriosclerosis, Thrombosis, and Vascular Biology, pp. 1788-1795, vol. 27, No. 8, Aug. 2007.
NCBI, GenBank accession No. NP_001090129.1, Aug. 16, 2011.
NCBI, GenBank accession No. EDN64809.1, Jul. 13, 2007.
NCBI, GenBank accession No. YP_788153.1, Apr. 15, 2009.
Kim, Seung Beon, International Search Authority and Written Opinion, PCT/US2013/051839, Korean International Property Office, Nov. 21, 2013.
Nickitas-Etienne, Athina, International Preliminary Report on Patentability and Written Opinion, PCT/US2013/051839, The International Bureau of WIPO, Feb. 5, 2015.

* cited by examiner

*Primary Examiner* — Jacob Cheu
(74) *Attorney, Agent, or Firm* — Joseph R. Baker, Jr.; Gavrilovich, Dodd & Lindsey LLP

(57) ABSTRACT

Provided herein are compositions and methods for examining the progression, regression or risk of individuals for having a stroke, transient ischemic attack or peripheral artery disease.

16 Claims, 6 Drawing Sheets

US 9,347,959 B2

OXIDATIVE BIOMARKERS IN PREDICTING RISK OF STROKE, TRANSIENT ISCHEMIC ATTACK (TIA) AND PERIPHERAL ARTERIAL DISEASE (PAD)

CROSS REFERENCE TO RELATED APPLICATIONS

This application is a U.S. National Stage Application filed under 35 U.S.C. §371 and claim priority to International Application No. PCT/US2013/051839, filed Jul. 24, 2013, which application claims priority to U.S. Provisional Application Ser. No. 61/675,164 filed Jul. 24, 2012, the disclosures of which are incorporated herein by reference.

TECHNICAL FIELD

Compositions and methods for identifying and predicting stroke and transient ischemic attack (TIA) are provided.

BACKGROUND

Atherosclerosis is initiated early in human life in an occult manner due to a variety of genetic, environmental and behavioral risk factors and is the leading cause of cardiovascular disease (CVD) events. It originates by the generation of subintimal macrophage foam cells that arise mainly due to the accumulation of oxidized lipids through unregulated uptake by macrophage scavenger receptors, an arm of the innate immune response in removing toxic substances to protect the host. After a long latent period of integrative and detrimental insults to the vessel wall, such as oxidation and chronic inflammation, it manifests clinically as either symptomatic obstructive disease such as angina or claudication, or acute atherothrombosis such as myocardial infarction and ischemic stroke.

Various degrees of subclinical atherosclerosis are almost universally present in people living in Western societies. However, the assessment of the specific future risk that subclinical atherosclerosis confers is difficult to assess at the individual level, even with invasive and expensive testing. This is due to the variable nature of its clinical expression, which is in part a consequence of the qualitative differences in plaque components in similar sized lesions. Furthermore, the current clinical paradigm of treating asymptomatic patients is appropriately focused on treating underlying risk factors and is not generally centered on treating only those patients with documented presence of atherosclerosis. In addition, aside from hypolipidemic therapies, specific treatments that target pathogenic mechanisms leading to clinical events, such as the oxidative, immune and inflammatory components, do not yet exist.

SUMMARY

The disclosure provides a method for determine a risk of stroke, a transient ischemic attack (TIA) or peripheral arterial disease (PAD) in a subject, the method comprising: a) obtaining a sample comprising plasma from a subject; b) determining the level of IgG and/or IgM autoantibodies to oxidation specific epitopes (OSEs); c) comparing the levels of IgG and/or IgM autoantibodies to OSEs in the sample to values of IgG and/or IgM autoantibodies indicative of high risk of stroke, TIA or PAD, wherein if the value of the IgG and/or IgM from the sample falls within the values of associated with high risk of stroke or TIA, the value is indicative of the risk of stroke, TIA or PAD in the subject. In another embodiment, the method further comprises determining the level of OxPL detectable on apoB-100 containing lipoproteins in the sample; and comparing the amount of OxPL on apoB obtained from the sample with values from low-risk, medium-risk and high-risk population values, wherein if the level of OxPL of the subject falls within the levels of subject with high risk of stroke, TIA or PAD, the level of the subject is predictive for the risk of stroke, TIA or PAD in the subject. In another embodiment, the determining the level of IgG and/or IgM autoantibodies comprises contacting the sample with an antigen that is recognized by the IgG and/or IgM autoantibodies. In yet a further embodiment, the antigen comprises a mimotope that is recognized by IgG and/or IgM autoantibodies to OxPL. In a further embodiment, the mimotope is selected from the group consisting of: (a) a linear peptide having a sequence of the general formula $X_1X_2X_3X_4X_5X_6X_7X_8X_9X_{10}X_{11}X_{12}$ (SEQ ID NO:1), wherein $X_1$ is an amino acid selected from the group consisting of N, E, Q, A, H, T, G, and D; $X_2$ is an amino acid selected from the group consisting of S, N, V, R, A, W, Y, and D; $X_3$ is an amino acid selected from the group consisting of W, R, Y, M, I, L, V, G, T, and P; $X_4$ is an amino acid selected from the group consisting of T, N, S, and F; $X_5$ is an amino acid selected from the group consisting of N, K, and S; $X_6$ is an amino acid selected from the group consisting of A, N, S, D, W, L, Y, T, I, V, K, and P; $X_7$ is an amino acid selected from the group consisting of S, W, D, T, A, Q, M, E, and P; $X_8$ is an amino acid selected from the group consisting of L, Q, A, V, G, M, H, S, E, and N; $X_9$ is an amino acid selected from the group consisting of S, W, H, M, L, A, E, T, D, Q, and R; $X_{10}$ is an amino acid selected from the group consisting of T, Y, R, S, Q, L, F, V, A, D, and I; $X_{11}$ is an amino acid selected from the group consisting of F, I, H, L, M V, and P; and $X_{12}$ is an amino acid selected from the group consisting of H, Q, G, S, M, A, P, W, and L; and (b) a cyclic peptide having a sequence with the general formula $X_1X_2X_3X_4X_5X_6X_7$ (SEQ ID NO:2), wherein $X_1$ is selected from the group consisting of N, K, Q, and D; $X_2$ is selected from the group consisting of N and W; $X_3$ is selected from the group consisting of W, R, Y, Q, S, and A; $X_4$ is selected from the group consisting of N, K, H, and P; $X_5$ is selected from the group consisting of M, Q and H; $X_6$ is selected from the group consisting of P, R and F; and $X_7$ is selected from the group consisting of L and T. In yet a further embodiment, the mimotope of part (a) comprises a sequence selected from the group consisting of: NSWTNASLSTFH (SEQ ID NO:3), NSRTNNSQWTFQ (SEQ ID NO:4), ESWTNSWAHYFG (SEQ ID NO:5), ESWTNSWAMYFG (SEQ ID NO:6), QSYTNDDVLRIS (SEQ ID NO:7), QNMNNWTLASIM (SEQ ID NO:8), EVMNNWTLASIM (SEQ ID NO:9), ASISNLTLSRFM (SEQ ID NO:10), HSWSNYWGHQHA (SEQ ID NO:11), HRISNYAMELHS (SEQ ID NO:12), HSLTNTQMTQLS (SEQ ID NO:13), HSLSNIQMATLA (SEQ ID NO:14), HRMTNAMHHFMG (SEQ ID NO:15), HRMTNNAMDVFM (SEQ ID NO:16), HRLTNSEQAALP (SEQ ID NO:17), TAVTNSMMERLW (SEQ ID NO:18), GWGNKTPSQDVH (SEQ ID NO:19), DYTNSVSMRYLS (SEQ ID NO:20), HQLSNKDEQTPQ (SEQ ID NO:21), and ADPFSPTNRIPL (SEQ ID NO:22). In yet a still further embodiment, the mimotope of part (a) comprises a sequence HSWTNSWMATFL (SEQ ID NO:23). In another embodiment, the mimotope of part (b) comprises a sequence selected from the group consisting of NNWNMPL (SEQ ID NO:24); NNRNMPL (SEQ ID NO:25); NNYNMPL (SEQ ID NO:26); NNQNMPL (SEQ ID NO:27); NNWKMPL (SEQ ID NO:28); NNSHMPL (SEQ ID NO:29); KNSXQPL (SEQ ID NO:30); NNSXMPL (SEQ ID NO:31); QNSHMPL (SEQ ID NO:32); NNSNMPL (SEQ ID NO:35); NNSKMRL (SEQ ID NO:33); and DWAPHFT (SEQ ID NO:34). In yet a further embodiment, the mimotope of part (b) is a cyclic peptide containing a sequence NNSN-MPL (SEQ ID NO:35). In yet further embodiments of the foregoing the mimotope further comprises from 1-10 additional amino acids at either then N-terminal or C-terminal ends. In another embodiment, the antigen comprises MDA-OxPL. In yet a further embodiment, the antigen comprises a OxPL selected from the group consisting of 1-palmitoyl-2-arachidonoyl-sn-glycero-3phos-phorylcholine (Ox-PAPC), 1-palmitoyl-2-oxovaleroyl-sn-glycero-3-phosphoryl-choline (POVPC), 1-palmitoyl-glutaroyl-sn-glycero-3-phosphorylcholine (PGPC), 1-palmitoyl-2-epoxyisoprostane-sn-glycero-3-phosphorylcholine (Ox-SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEIPE). In another embodiment, the level of OxPL and the level of total apoB-100 in the sample are measured with two or more different antibodies, wherein a first antibody specifically interacts with OxPL and a second antibody specifically interacts with apoB-100. In one embodiment, the antibodies are monoclonal antibodies. In a further embodiment, the antibody that interacts with OxPL is E06 or DLH3. In yet other embodiments, any one of the foregoing the method further comprises correlating the value or ratio for the subject with: a) the age of the subject at the time the sample is obtained; b) the subject's gender; and/or c) the subject's race. In yet other embodiments, of any one of the foregoing the method further comprises correlating the value or ratio for the subject with other risk factors selected from the group consisting of current smoking, hypertension, LDL cholesterol levels, and triglyceride levels. In another embodiment, the method further comprises determining the level of Lp(a) lipoprotein from the sample and comparing the Lp(a) lipoprotein level for the subject with Lp(a) lipoprotein levels from subjects at high risk or with documented CAD, ACS, or at risk for ACS, wherein if the Lp(a) lipoprotein level for the subject falls within the Lp(a) lipoprotein level range from subjects at high risk or with documented CAD, ACS, or at risk for ACS, is predictive for the risk of stroke or TIA in the subject. In one embodiment, if the IgG levels fall within the upper tertile of values from a general population, then the subject is at risk for CVD, TIA or stroke. In another embodiment, if IgM levels fall within the lower tertile of values from a general population, then the subject is at risk for CVD, TIA or stroke. In another embodiment, the samples are obtained at two different time points. In yet another embodiment, the IgM and/or IgG levels are compared between a current and prior measurement of IgM and/or IgG levels, wherein an increase in IgM levels is indicative of a reduced risk of CVD, stroke or TIA.

The disclosure provides a method for determine a risk of stroke, TIA or PAD in a subject, the method comprising: a) obtaining a sample comprising plasma from a subject; b) determining one or more biomarkers of cardiac disease, stroke, TIA or PAD, wherein at least one biomarker comprises the level of IgG and/or IgM to OSEs wherein if the value of the biomarker or biomarker panel falls within the values of subject with high risk of stroke, TIA or PAD, the values of the subject is predictive for the risk of stroke, TIA or PAD in the subject. In one embodiment, the level of OxPL on apoB-100 in the sample are measured with two or more different antibodies, wherein a first antibody specifically interacts with OxPL and a second antibody specifically interacts with apoB-100. In one embodiment, an antibody to apoB is bound to a substrate and the sample is contacted with the substrate, the substrate is then washed and a second, labeled antibody against OxPL is then contacted with the substrate comprising bound apoB. The amount of OxPL antibody bound to OxPL associated with apoB are then determined. In another embodiment, the antibodies are monoclonal antibodies. In yet another embodiment, the antibody that interacts with OxPL is E06 or DLH3 or other antibody binding OxPL. In a specific embodiment, the subject is human. In another embodiment, the oxidized phospholipid is selected from the group consisting of oxidized forms of 1-palmitoyl-2-arachidonoyl-sn-glycero-3-phos-phorylcholine (Ox-PAPC), 1-palmitoyl-2-oxovaleroyl-sn-glycero-3-phosphoryl-choline (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), oxidized 1-stearoyl-2-arachidonyl-sn-glycero-3-phosphorylcholine (Ox-SAPC), 1-stearoyl-2-oxovaleroyl-sn-glycero-3-phosphorylcholine (SOVPC, 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEIPE). In yet a further embodiment, the ratio for the subject is further correlated with: a) the age of the subject at the time the sample is obtained; b) the subject's gender; and/or c) the subject's race. In yet another embodiment, the method includes correlating the ratio for the subject with other risk factors selected from the group consisting of current smoking, hypertension, LDL cholesterol levels, and triglyceride levels. In another embodiment, the method further comprises determining the level of Lp(a) lipoprotein from the sample and comparing the Lp(a) lipoprotein level for the subject with Lp(a) lipoprotein levels from subjects at high risk or with documented CAD, ACS, or at risk for ACS, wherein if the Lp(a) lipoprotein level for the subject falls within the Lp(a) lipoprotein level range from subjects at high risk or with documented CAD, ACS, or at risk for ACS, is predictive for the risk of stroke or TIA in the subject. In yet a further embodiment, the method further comprises measuring IgM and/or IgG levels of antibodies in the subject's serum that interact with oxidized phospholipids. In any of the foregoing embodiments, the ratios and measurements are made at two different time points for the same subject. In a further embodiment, the IgM and/or IgG levels are compared between a current and prior measurement of IgM and/or IgG levels, wherein an increase in IgM levels is indicative of a reduced risk of stroke or TIA. In yet another embodiment, the method includes correlating the Lp(a) lipoprotein levels from the subject with other atherogenesis risk factors selected from the group consisting of current smoking, hypertension, LDL cholesterol levels, and triglyceride levels.

The method of any of the foregoing, wherein a subject is classified or reclassified into higher or lower risk categories by measuring OxPL/apoB and IgG and IgM autoantibodies to OSE. A method of using a combination of OxPL/apoB levels and IgM and/or IgG levels to enhance clinical risk predications. A method of measuring a combination of the above biomarkers to provide better predictive value than measuring one or the other alone.

The details of one or more embodiments of the disclosure are set forth in the accompanying drawings and the description below. Other features, objects, and advantages will be apparent from the description and drawings, and from the claims.

DETAILED DESCRIPTION

Figure 1A:
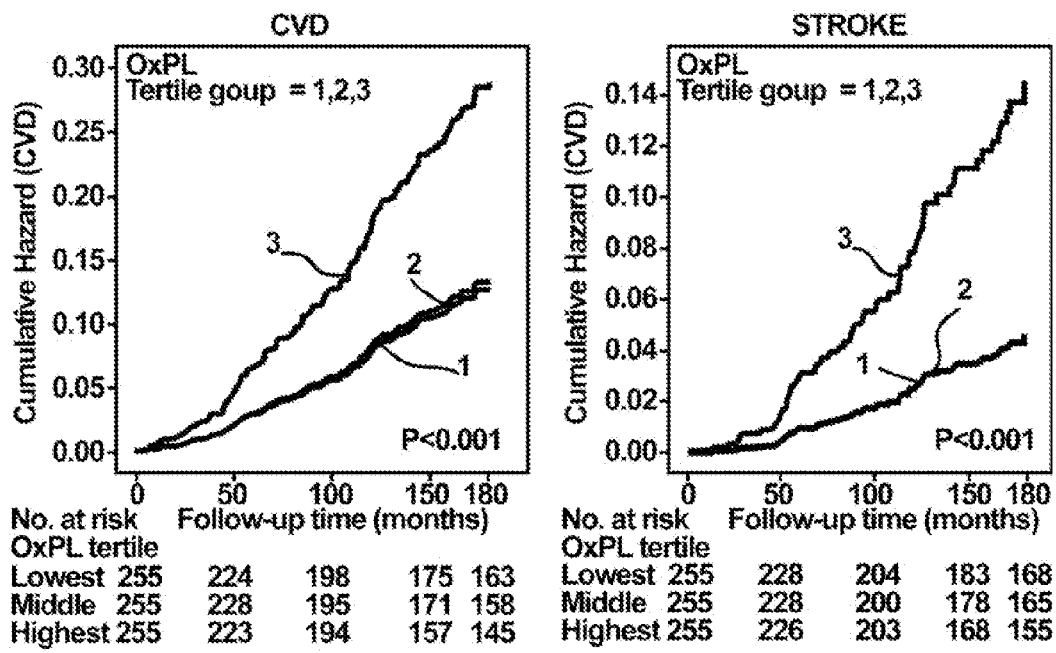
FIG. 1A-B show OxPL/apoB values. (a) shows cumulative hazard curves for cardiovascular disease (CVD) incidence and stroke incidence by OxPL tertile groups. The median OxPL/apoB level (RLU) for the lowest tertile was 2908 (range, 1584-3631); for the middle tertile, 4862 (range, 3632-8124); and for the highest tertile, 18830 (range, 8125-79541). There were 138 cases of incident cardiovascular disease and 60 cases of incident stroke in this population sample. (b) Levels of oxidized phospholipid/apoB and lipoprotein(a) categorized by racial group; Boxes indicate medians, 25th and 75th percentile, whiskers indicate 10th and $90^{th}$ percentile. Differences among racial groups are all significant (p<0.001). BF: Black females; BM: Black males; HF: Hispanic females; HM: Hispanic males; OxPL: Oxidized phospholipid; RLU: Relative light units; WF: White females; WM: White males.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

A key problem in treating vascular diseases is proper diagnosis. Often the first sign of the disease is sudden death. For example, approximately half of all individuals who die of coronary artery disease die suddenly. Furthermore, for 40-60% of the patients who are eventually diagnosed as having coronary artery disease, myocardial infarction is the first presentation of the disease. Unfortunately, approximately 40% of those initial events go unnoticed by the patient.

Inflammation is now generally regarded as an important component of the pathogenic process of atherosclerosis (Munro, Lab Invest., 58:249-261 (1988); Badimon, et al., Circulation, 87:3-16 (1993); Liuzzo, et al., N. E. J. M., 331(7):417-24 (1994); Alexander, N. E. J. M., 331(7):468-9 (1994)).

Several inflammatory products, including IL-1 beta, have been identified in atherosclerotic lesions or in the endothelium of diseased coronary arteries (Galea, et al., Ath. Thromb. Vasc. Biol., 16:1000-6 (1996)). Also, serum concentrations of IL-1 beta have been found to be elevated in patients with coronary disease (Hasdai, et al., Heart, 76:24-8 (1996)). In addition, oxidized phospholipids (OxPL) are pro-inflammatory and can be detected by monoclonal antibody E06 on apolipoprotein B-100 particles (OxPL/apoB), and primarily on Lp(a) lipoprotein [Lp(a)].

Lp(a) is associated with enhanced atherogenic potential, particularly at levels >30 mg/dl, and has generally been shown to be an independent predictor (odds ratio ~1.5-2) of cardiovascular risk, particularly in younger subjects (<60 years old) and those with elevated LDL cholesterol levels. Since it appears that the atherogenicity of Lp(a) may be mediated in part by its association with OxPL. Cells loaded with cholesterol ester in the arteries cause the characteristic 'fatty streak' associated with the early stages of atherosclerosis.

Plasma biomarkers of cardiovascular disorder (CVD), stroke and acute ischemic injury are useful in diagnosing and prognosing a subject's risk and potential treatment. In particular, biomarkers that function as a link between risk factors and clinical CVD and are also putatively involved in casual pathways of atherosclerosis are an attractive addition to the clinical armamentarium. Oxidation-specific epitopes (OSE), present in plasma on circulating lipoproteins and lipoprotein (a) {Lp(a)} and in the vessel wall on lipoproteins, apoptotic cells and matrix proteins, are strong candidates as potentially causal biomarkers more proximal to the atherosclerotic disease process. OSEs represent "danger-associated molecular patterns (DAMPs)" that are pro-inflammatory and are integrally involved in oxidative, innate and adaptive immune responses. Biomarkers as described herein are useful for identifying CVD, stroke, TIA, or PAD risk.

Acute ischemic stroke is estimated to affect ~2-2.5 out of every thousand people, resulting upwards of 4.5 million deaths per year worldwide and 9 million stroke survivors, with costs currently exceeding $50 billion in the U.S. alone. Strokes, or cerebrovascular accidents, are the result of an acute obstruction of cerebral blood flow to a region of the brain. There are approximately 500,000 cases each year in the United States, of which 30% are fatal, and hence stroke is the third leading cause of death in the United States. Approximately 80% of strokes are "ischemic" and result from an acute occlusion of a cerebral artery with resultant reduction in blood flow. The remainder are "hemorrhagic", which are due to rupture of a cerebral artery with hemorrhage into brain tissue and consequent obstruction of blood flow due to lack of flow in the distal region of the ruptured vessel and local tissue compression, creating ischemia.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

A "cardiovascular disease" is a cardiovascular disorder, as defined herein, characterized by clinical events including clinical symptoms and clinical signs. Clinical symptoms are those experiences reported by a patient that indicate to the clinician the presence of pathology. Clinical signs are those objective findings on physical or laboratory examination that indicate to the clinician the presence of pathology. "Cardiovascular disease" includes both "coronary artery disease" and "peripheral vascular disease." Clinical symptoms in cardiovascular disease include chest pain, shortness of breath, weakness, fainting spells, alterations in consciousness, extremity pain, paroxysmal nocturnal dyspnea, transient ischemic attacks and other such phenomena experienced by the patient. Clinical signs in cardiovascular disease include such findings as EKG abnormalities, altered peripheral pulses, arterial bruits, abnormal heart sounds, rales and wheezes, jugular venous distention, neurological alterations and other such findings discerned by the clinician. Clinical symptoms and clinical signs can combine in a cardiovascular disease such as a myocardial infarction (MI) or a stroke (also termed a "cerebrovascular accident" or "CVA"), where the patient will report certain phenomena (symptoms) and the clinician will perceive other phenomena (signs) all indicative of an underlying pathology. "Cardiovascular disease" includes those diseases related to the cardiovascular disorders of fragile plaque disorder, occlusive disorder and stenosis. For example, a cardiovascular disease resulting from a fragile plaque disorder, as that term is defined below, can be termed a "fragile plaque disease." Clinical events associated with fragile plaque disease include those signs and symptoms where the rupture of a fragile plaque with subsequent acute thrombosis or with distal embolization are hallmarks. Examples of fragile plaque disease include certain strokes and myocardial infarctions. As another example, a cardiovascular disease resulting from an occlusive disorder can be termed an "occlusive disease." Clinical events associated with occlusive disease include those signs and symptoms where the progressive occlusion of an artery affects the amount of circulation that reaches a target tissue. Progressive arterial occlusion may result in progressive ischemia that may ultimately progress to tissue death if the amount of circulation is insufficient to maintain the tissues. Signs and symptoms of occlusive disease include claudication, rest pain, angina, and gangrene, as well as physical and laboratory findings indicative of vessel stenosis and decreased distal perfusion. As yet another example, a cardiovascular disease resulting from restenosis can be termed an in-stent stenosis disease. In-stent stenosis disease includes the signs and symptoms resulting from the progressive blockage of an arterial stent that has been positioned as part of a procedure like a percutaneous transluminal angioplasty, where the presence of the stent is intended to help hold the vessel in its newly expanded configuration. The clinical events that accompany in-stent stenosis disease are those attributable to the restenosis of the reconstructed artery.

A "cardiovascular disorder" refers broadly to both coronary artery disorders and peripheral arterial disorders. The term "cardiovascular disorder" can apply to any abnormality of an artery, whether structural, histological, biochemical or any other abnormality. This term includes those disorders characterized by fragile plaque (termed herein "fragile plaque disorders"), those disorders characterized by vaso-occlusion (termed herein "occlusive disorders"), and those disorders characterized by restenosis. A "cardiovascular disorder" can occur in an artery primarily, that is, prior to any medical or surgical intervention. Primary cardiovascular disorders include, among others, atherosclerosis, arterial occlusion, aneurysm formation and thrombosis. A "cardiovascular disorder" can occur in an artery secondarily, that is, following a medical or surgical intervention. Secondary cardiovascular disorders include, among others, post-traumatic aneurysm formation, restenosis, and post-operative graft occlusion.

A "coronary artery disease" ("CAD") refers to a vascular disorder relating to the blockage of arteries serving the heart. Blockage can occur suddenly, by mechanisms such as plaque rupture or embolization. Blockage can occur progressively, with narrowing of the artery via myointimal hyperplasia and plaque formation. Those clinical signs and symptoms resulting from the blockage of arteries serving the heart are manifestations of coronary artery disease. Manifestations of coronary artery disease include angina, ischemia, myocardial infarction, cardiomyopathy, congestive heart failure, arrhythmias and aneurysm formation. It is understood that fragile plaque disease in the coronary circulation is associated with arterial thrombosis or distal embolization that manifests itself as a myocardial infarction. It is understood that occlusive disease in the coronary circulation is associated with arterial stenosis accompanied by anginal symptoms, a condition commonly treated with pharmacological interventions and with angioplasty.

The term "interact" as used herein is meant to include detectable relationships or associations (e.g. biochemical interactions) between molecules, such as interactions between protein-protein, protein-lipid, protein-nucleic acid, and the like.

The term "marker" refers to a sequence or a biological factor in the genome or subject that is known to vary among individuals and can be associated with a particular disease or disease risk.

"PAD" or "peripheral artery disease" encompasses disease states such as atherosclerosis and atherothrombosis that occur outside the heart and brain. It is a common comorbid disease with CAD. Subjects who are deemed to be at low risk or no risk of PAD based upon an assessment of traditional risk factors of PAD (or arteriovascular disease), or who are asymptomatic for PAD or an arteriovascular disease may nevertheless be at risk for an arteriovascular event, even in the absence of claudication. Claudication can be defined as pain or discomfort in the muscles of the legs occurring due to a decreased amount of blood flowing to a muscle from narrowing of the peripheral arteries, producing ischemia and often arterial occlusion, causing skeletal muscle and limb necrosis. The pain or discomfort often occurs when walking and dissipates under resting conditions (intermittent claudication). Pain, tightness, cramping, tiredness or weakness is often experienced as a result of claudication. PAD not only causes the hemodynamic alterations common in CAD, but also results in metabolic changes in skeletal muscle. When PAD has progressed to severe chronic and acute peripheral arterial occlusion, surgery and limb amputation often become the sole therapeutic options. PAD is widely considered to be an underdiagnosed disease, with the majority of confirmed diagnoses occurring only after symptoms are manifested, or only with other arteriovascular disease, and irreversible arteriovascular damage due to such ischemic events has already occurred.

In the context of the disclosure, "population" refers to any selected group of individuals, such as individuals that live in a particular geographic region, country or state. In some cases, the population is a group of subjects, such as a group of subjects that participated in a clinical study. In another embodiment, a population can comprise an ethnic group, an age group or can be based on sex. In particular examples, the population is the Framingham Offspring Cohort.

The term "propensity to disease," also "predisposition" or "susceptibility" to disease or any similar phrase, means that certain markers are associated with or predictive of a subject's incidence of developing a particular disease (herein, a cardiovascular disease). The biomarker (e.g., the presence of a particular ratio or level of phospholipid or apoprotein) are thus over-represented or underexpressed (depending upon the marker) in frequency in individuals with disease as compared to healthy individuals.

A "risk factor" is a factor identified to be associated with an increased risk. A risk factor for a stroke or cardiovascular disorder or a cardiovascular disease is any factor identified to be associated with an increased risk of developing those conditions or of worsening those conditions. A risk factor can also be associated with an increased risk of an adverse clinical event or an adverse clinical outcome in a patient with a cardiovascular disorder. Risk factors for cardiovascular disease include smoking, adverse lipid profiles, elevated lipids or cholesterol, diabetes, hypertension, hypercoagulable states, elevated homocysteine levels, and lack of exercise. Carrying a particular polymorphic allele is a risk factor for a particular cardiovascular disorder, and is associated with an increased risk of the particular disorder.

The term "treating" as used herein is intended to encompass curing as well as ameliorating at least one symptom of a disease or at least one abnormality associated with a disorder. Treating a cardiovascular disorder can take place by administering a cardiovascular disorder therapeutic. Treating a cardiovascular disorder can also take place by modifying risk factors that are related to the cardiovascular disorder.

A "treatment plan" refers to at least one intervention undertaken to modify the effect of a risk factor upon a patient. A treatment plan for a cardiovascular disorder or disease can address those risk factors that pertain to cardiovascular disorders or diseases. A treatment plan can include an intervention that focuses on changing patient behavior, such as stopping smoking. A treatment plan can include an intervention whereby a therapeutic agent is administered to a patient. As examples, cholesterol levels can be lowered with proper medication, and diabetes can be controlled with insulin. Nicotine addiction can be treated by withdrawal medications. A treatment plan can include an intervention that is diagnostic. The presence of the risk factor of hypertension, for example, can give rise to a diagnostic intervention whereby the etiology of the hypertension is determined. After the reason for the hypertension is identified, further treatments may be administered.

The clinical role of autoantibodies to OxLDL has progressively evolved since the first demonstration of their presence in human and animal experimental lesions over 20 years ago. This area has been controversial due to mixed results arising for a variety of factors related to lack of prospective studies, small cohorts, lack of adequate power and extended follow-up. In addition, there has been a lack of standardization of antigens to precisely measure their level in comparative studies.

Figure 1B:
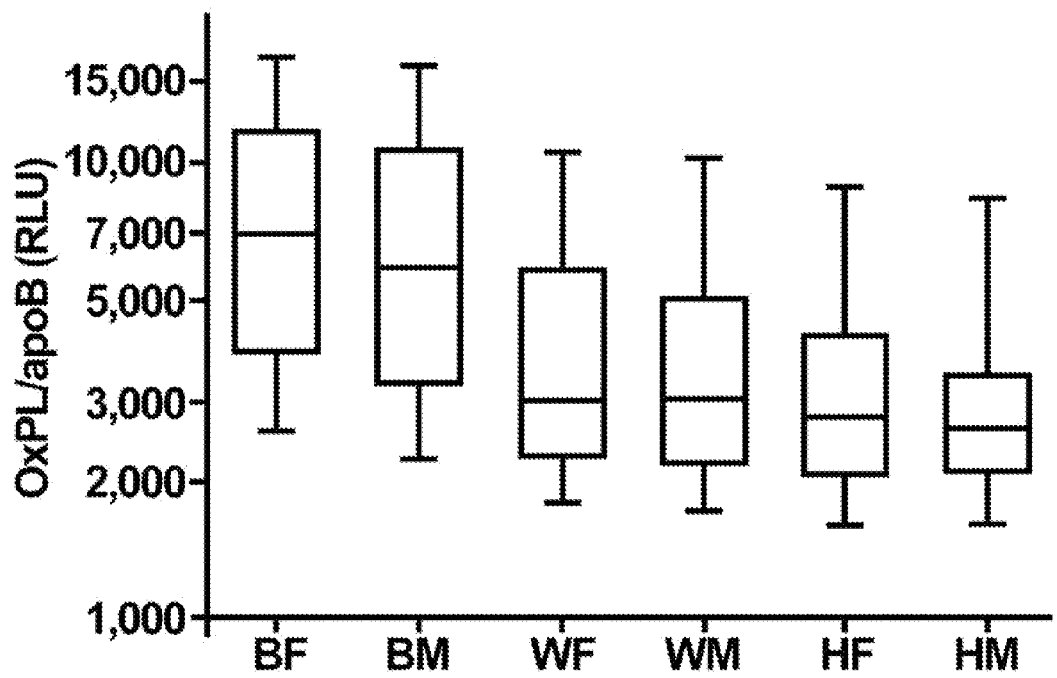

The disclosure demonstrates the OxPL/apoB levels are predictor of stroke, TIA and PAD. The data demonstrate that high levels of OxPL/apoB are indicative of a predisposition or likelihood of recurrence of stroke, TIA or PAD when compared to a population of normal values. With reference to FIG. 1B there are shown values of OxPL/apoB for various ethnic backgrounds. Using these values for example, subject that fall within the higher quartile have a risk of stroke, TIA and/or PAD. Furthermore, subjects that remain at highlevels after the occurrence of a stroke, TIA and/or PAD have an increased risk of recurrent stroke, TIA and/or PAD.

The disclosure demonstrates the clinical value of oxidation-specific biomarkers in predicting CVD events. The disclosure demonstrates that OxPL/apoB and/or IgG Cu-OxLDL autoantibodies predicted a higher event rate of CVD, whereas IgM Cu-OxLDL autoantibodies predicted a lower event rate of CVD. Thus, these biomarkers improve the predictive accuracy of CVD events. Using these biomarkers in a model adjusting for 13 clinical variables, including hsCRP, the biomarkers allowed reclassification of subjects at initial low, intermediate and high-risk categories, moving a significant number of subjects into both higher and lower categories. The data presented herein are based, in part, on the Bruneck population study. The Bruneck population study reflects individuals seen in a primary care setting, which allows broad application of oxidation-specific biomarkers in addition to currently available clinical and laboratory risk factors to allow optimal risk prediction and tailored therapies to appropriately match the risk with the intensity of treatment and follow-up.

The disclosure relates to the analysis of OxPL/apoB levels of patients at high risk, suspected to be at risk for or under treatment for a cardiovascular disease, stroke, TIA and/or PAD. The cardiovascular disease, stroke risk, TIA and/or PAD can be associated with high cholesterol or LDL levels. The methods and compositions of the disclosure are useful for diagnostic purposes and for monitoring the effects of dietary interventions, as well as for monitoring treatment for reducing cholesterol and high LDL levels using drugs such as statins or other interventions for the treatment of stroke and/or TIA. More particularly, the disclosure relates to methods and compositions useful for determining the levels of IgG and/or IgM autoantibodies to OSE in a subject as indices of stroke and transient ischemic attack (TIA) or PAD.

The disclosure supports the unifying hypothesis that OSEs, such as OxPL and MDA epitopes, represent DAMPs that are detrimental to the host, and that the innate immune system provides protective responses to them. Such DAMPs are strongly present on apoptotic cells, infectious pathogens such as pneumococcus and oxidized lipids. In response to such DAMPs, evolutionary processes have preserved and amplified innate immune effector proteins to bind and neutralize their pro-inflammatory effects. The initial evolutionary pressure may have been derived from the need to clear trillions of apoptotic cells on a daily basis, which may have been subsequently amplified by repeated exposure to common infectious pathogens that share similar epitopes or molecular mimics, as well as oxidized lipids derived from the diet and those generated in vivo following oxidative stress in the setting of dyslipidemia and other risk factors. These innate effector proteins are represented by a variety of macrophage scavenger receptors, IgM natural antibodies such as E06 and IgM autoantibodies measured in this study, as well as innate plasma proteins, such as CRP, which binds not only the phosphocholine (PC) headgroup of OxPL, but the same PC (not as part of a PL) on the cell wall of Streptococcal pneumonia.

The disclosure further demonstrates that increased baseline levels of IgG autoantibodies to Cu-OxLDL OSEs predict higher risk of cardiovascular events. In contrast, IgM autoantibodies to OSEs were associated with lower incident CVD event rates and stroke. These data suggest that IgM autoantibodies may be atheroprotective. Consistent with this interpretation is that (a) IgM OxLDL autoantibodies are highest in younger patients and decline as patients age, when CVD risk is highest; (b) OSE represent a dominant, previously unrecognized target of IgM natural antibodies in both mice and humans and that ~30% of all natural antibodies bind to model OSE, atherosclerotic lesions, and apoptotic cells—the high prevalence of such OSE-specific natural antibodies suggests strong evolutionary pressure in protecting hosts for pro-inflammatory effects of OSE; (c) the natural antibody IgM E06/T15 has the capacity to block macrophage uptake of OxLDL, and generation of high titers of E06 in response to pneumococcal vaccination in cholesterol-fed LDLr$^{-/-}$ mice results in reduced atherosclerosis; and (d) direct experimental evidence for a protective role of IgM autoantibodies in several different murine models of atherosclerosis: for example, the demonstration that the complete absence of B-1 cell-derived IgM led to accelerated atherosclerosis in Ldlr$^{-/-}$ mice, and transfer of B-1 cells capable of secreting IgM into splenectomized apoE$^{-/-}$ mice was atheroprotective, but transfer of B-1 cells incapable of secreting IgM was not. This data suggests that natural IgM antibodies are evolutionarily selected in nature and play an important role in mediating homeostatic functions. In the case of CVD, the presence of circulating IgM may lead to prevention of foam cell formation, as has been shown with passive immunization of human antibodies, and neutralization and/or clearance of apoptotic cells and other OSE when generated by oxidative stress. In this way, they provide a beneficial innate immune function when DAMPs are generated.

The OxPL/apoB levels can be used alone or may be combined with other diagnostic biomarkers (e.g., IgG and/or IgM autoantibodies to OSEs, Lp(a) values and the like). For example, and as described in more detail below, a plasma or blood sample can be obtained from a subject and the amount OxPL on apoB quantified. In addition, this same sample can be analyzed for IgG autoantibodies to OSEs. The OxPL/apoB leves and the IgG autoantibodies levels in the sample can be compared to values in a population of low-risk subjects, wherein if the levels in the sample is elevated compared to the low-risk population the subject can be identified as an "at-risk" subject for CVD, ischemia, TIA and/or PAD. Alternatively, the values can be compared to a standard comprising values obtained from low-risk and high-risk subjects. More particularly, if the levels in the test sample is elevated by at least 10%, 20%, 30%, 40%, 50%, 60%, 70%, 80%, 90%, 95% or more compared to the low-risk population levels, then the subject from which the samples was obtained is identified as an at-risk subject. In this embodiment, the level of IgG autoantibodies to OxPL can be measured using naturally occurring antigens or non-naturally occurring antigens that are recognized by the IgG autoantibodies. For examples, methods of making artificial OxPLs are known in the art. In addition, mimotopes that are recognized by IgG autoantibodies, as described below, can be used. Various assay methods can be used including, for example, standard sandwich assays. Typically either the antigen is labeled or a secondary antibody is labeled (e.g., an antibody against the IgG).

In another embodiment, either alone or in combination with the foregoing measurements, a plasma or blood sample can be obtained from a subject and the amount of IgM autoantibodies to OSEs identified. The amount of IgM autoantibodies in the sample can be compared to IgM levels from a population of low-risk and/or high-risk subjects and wherein if the level of IgM in the sample is elevated compared to the high-risk population the subject can be identified as a "low-risk" subject for CVD, stroke and/or TIA. Alternatively, where the IgM levels are similar to levels found in a population of low-risk subjects, then the subject from which the sample was obtained can be identified as "low-risk". More particularly, if the level of IgM in the test sample is elevated by at least 10%, 20%, 30%, 40%, 50%, 60%, 70%, 80%, 90%, 95% or more compared to the high-risk population levels, then the subject from which the samples was obtained is identified as a low-risk subject. In this embodiment, the level of IgM autoantibodies to OSEs can be measured using naturally occurring antigens or non-naturally occurring antigens/epitopes that are recognized by the IgM autoantibodies. For examples, methods of making artificial OxPLs are known in the art. In addition, mimotopes as described below can be used. Various assay methods can be used including, for example, standard sandwich assays. Typically either the antigen is labeled or a secondary antibody is labeled (e.g., an antibody against the IgM).

Assays for determining OxPL/apoB are also provides For example, the assay can comprise a chemiluminescent ELISA to detect OxPL on human apoB-100 (OxPL/apoB)-containing lipoprotein particles in plasma. The assay is performed by plating overnight murine monoclonal antibody MB47 (~50 μl at ~5 μg/ml), which captures a saturating amount of apoB-100 on all apoB-containing lipoproteins from plasma. After washing, the plates are coated with ~1% bovine serum albumin in tris-(hydroxymethyl) aminomethane-buffered saline. Plasma (~50 μl at 1:50 dilution) is added and allowed to incubate for 75 min. This initial step is designed so that each well captures a constant, saturating amount of apoB-100 from plasma and therefore normalizes the OxPL measure to an equal amount of apoB in the well for each patient. Thus, by definition, the OxPL/apoB measurement is independent of apoB and LDL cholesterol levels. Biotinylated E06 (~1 μg/ml) (or any other antibody that binds OxPL) is added and allowed to incubate for 1 h. Alkaline phosphatase neutravidin (1:40,000 dilution) is added for 1 h. Lumi-Phos® 530 (Lumigen, Inc., Southfield, Mich., USA; 25 μl) is added for 75 min to detect OxPL per unit of apoB captured (e.g., OxPL in relative light units [RLU]/apoB). Since an equal amount of apoB-100 is captured in each well from each subject, the denominator is the same in all wells (e.g., 1) and, thus, the actual read out is the amount of OxPL as detected by E06. This is detected by chemiluminescent technique and reported in RLU in 100 ms. The OxPL/apoB assay is highly specific to the number of OxPL epitopes on individual apoB-100 particles, but does not measure the total amount of OxPL in plasma.

Using the RLU values for OxPL/apoB, one can compare the RLU values to various standards indicative of risk, normal and low risk. For example, using FIG. 1B, one can compare the RLU from a test sample to the ethnic/race population. In addition, using the data in the figures the relative risk can be determined. Furthermore, subjects that experienced a stroke or had recurrent stroke had higher baseline OxPL/apoB, and had less decrease over time, including with atorvastatin treatment; although atorvastatin had some beneficial effects. A COX proportional hazard model analyses confirmed that baseline levels of OxPL/apoB was associated with the primary endpoint "stroke". In addition, a quartile analysis was used to illustrate the association between baseline OxPL/apoB and primary endpoint recurrent "stroke". The lowest level of OxPL/apoB (1st quartile) was associated with lower risk, while all other quartiles had relatively higher risk. Accordingly, the disclosure demonstrates that levels of OxPL/apoB higher than the first quartile are predictive of a first occurrence of stroke and that the values are also predictive of recurrent stroke.

Thus, the disclosure provides a method of determining the risk of stroke, TIA and/or PAD in a subject by determining the amount of OxPL on apoB, comparing the amount to standards for a subject's population criteria (e.g., Black, White, Male, Female and the like) and determining if the subject's OxPL/apoB values fall within a $1^{st}$, $2^{nd}$, $3^{rd}$, or $4^{th}$ quartile from low to high. If the subject's values fall with in the first quartile then the subject is at low risk for a first stroke, TIA and/or PAD event. If the subject's values fall within a $2^{nd}$ or beyond (i.e., $3^{rd}$ or $4^{th}$) quartile, then the subject's risk of stroke, TIA and/or PAD increases. Furthermore, if the subject has already had a stroke, TIA and/or PAD event then the values are also predictive of a risk of a second stroke, TIA and/or PAD. The levels of OxPL/apoB can be determined using any of the one or more assays described herein. In particularly, the assays can utilize non-naturally occurring antibodies such as labeled E06 antibodies, MB47 antibodies and the like. For example, in one embodiment the measuring of OxPL/apoB includes an antibody that interacts specifically with OxPL such as for example E06, T15 or DLH3 and an antibody that interacts specifically with apoB such as for example MB47 optionally a control OxPL sample.

To improve the fidelity of any risk determination, additional markers may be analyzed. For example, the disclosure further provides an in vitro assay that quantitates that amount of IgG and/or IgM autoantibodies to OxPL in a sample and correlates those values with standards to determine whether a subject is at high-risk, medium risk or low risk of CVD, stroke and/or TIA. These methods can be used in combination with other biomarker to evaluate CVD, stroke and/or TIA. For example, the assays described above can be used in combination with the measurement of OxPL/apoB levels, Lp(a) values, IL1-beta levels and the like.

The disclosure provides specific peptides that are immunological mimotopes for antibodies against OxPL. These mimotopes can serve as standardized and reproducible antigens that will be useful for diagnostic and therapeutic applications in cardiovascular disease.

The disclosure provides a peptide mimotope, wherein the peptide mimotope contains between about 7 and 12 amino acids and specifically binds a polyclonal or monoclonal antibody that is specific for an oxidation-specific epitopes (OSEs) on LDLs. In another embodiment of any of the foregoing, the peptide mimotope is selected from the group consisting of: (a) a linear peptide having a sequence of the general formula $X_1X_2X_3X_4X_5X_6X_7X_8X_9X_{10}X_{11}X_{12}$ (SEQ ID NO:1), wherein $X_1$ is an amino acid selected from the group consisting of N, E, Q, A, H, T, G, and D; $X_2$ is an amino acid selected from the group consisting of S, N, V, R, A, W, Y, and D; $X_3$ is an amino acid selected from the group consisting of W, R, Y, M, I, L, V, G, T, and P; $X_4$ is an amino acid selected from the group consisting of T, N, S, and F; $X_5$ is an amino acid selected from the group consisting of N, K, and S; $X_6$ is an amino acid selected from the group consisting of A, N, S, D, W, L, Y, T, I, V, K, and P; $X_7$ is an amino acid selected from the group consisting of S, W, D, T, A, Q, M, E, and P; $X_8$ is an amino acid selected from the group consisting of L, Q, A, V, G, M, H, S, E, and N; $X_9$ is an amino acid selected from the group consisting of S, W, H, M, L, A, E, T, D, Q, and R; $X_{10}$ is an amino acid selected from the group consisting of T, Y, R, S, Q, L, F, V, A, D, and I; $X_{11}$ is an amino acid selected from the group consisting of F, I, H, L, M V, and P; and $X_{12}$ is an amino acid selected from the group consisting of H, Q, G, S, M, A, P, W, and L; and (b) a cyclic peptide having a sequence with the general formula $X_1X_2X_3X_4X_5X_6X_7$ (SEQ ID NO:2), wherein $X_1$ is selected from the group consisting of N, K, Q, and D; $X_2$ is selected from the group consisting of N and W; $X_3$ is selected from the group consisting of W, R, Y, Q, S, and A; $X_4$ is selected from the group consisting of N, K, H, and P; $X_5$ is selected from the group consisting of M, Q and H; $X_6$ is selected from the group consisting of P, R and F; and $X_7$ is selected from the group consisting of L and T. In yet a further embodiment, the peptide of part (a) comprises a sequence selected from the group consisting of: NSWTNASLSTFH (SEQ ID NO:3), NSRTNNSQWTFQ (SEQ ID NO:4), ESWTNSWAHYFG (SEQ ID NO:5), ESWTNSWAMYFG (SEQ ID NO:6), QSYTNDDVLRIS (SEQ ID NO:7), QNMNNWTLASIM (SEQ ID NO:8), EVMNNWTLASIM (SEQ ID NO:9), ASISNLTLSRFM (SEQ ID NO:10), HSWSNYWGHQHA (SEQ ID NO:11), HRISNYAMELHS (SEQ ID NO:12), HSLTNTQMTQLS (SEQ ID NO:13), HSLSNIQMATLA (SEQ ID NO:14), HRMTNAMHHFMG (SEQ ID NO:15), HRMTNNAMDVFM (SEQ ID NO:16), HRLTNSEQAALP (SEQ ID NO:17), TAVTNSMMERLW (SEQ ID NO:18), GWGNKTPSQDVH (SEQ ID NO:19), DYTNSVSMRYLS (SEQ ID NO:20), HQLSNKDEQTPQ (SEQ ID NO:21), and ADPFSPTNRIPL (SEQ ID NO:22). In a specific embodiment, the peptide of part (a) comprises a sequence HSWTNSWMATFL (SEQ ID NO:23). In yet another embodiment, the peptide of part (b) comprises a sequence selected from the group consisting of NNWNMPL (SEQ ID NO:24); NNRNMPL (SEQ ID NO:25); NNYNMPL (SEQ ID NO:26); NNQNMPL (SEQ ID NO:27); NNWKMPL (SEQ ID NO:28); NNSHMPL (SEQ ID NO:29); KNSXQPL (SEQ ID NO:30); NNSXMPL (SEQ ID NO:31); QNSHMPL (SEQ ID NO:32); NNSNMPL (SEQ ID NO:35); NNSKMRL (SEQ ID NO:33); and DWAPHFT (SEQ ID NO:34). In a specific embodiment, the peptide of part (b) is a cyclic peptide containing a sequence NNSNMPL (SEQ ID NO:33). In another embodiment of any of the foregoing the peptide further comprising from 1-10 additional amino acids at either then N-terminal or C-terminal ends of the peptide.

The peptide mimotopes of the disclosure can be coated on a carrier for assaying the presence of IgG and/or IgM autoantibodies to OxPL. The disclosure also provides a peptide mimotope of the disclosure further comprising a detectable label. The labeled peptide mimotopes are useful in assays for detecting binding complexes with autoantibodies.

The disclosure also provides a method of detecting antibodies to OSEs comprising (a) contacting the substrate coated with a peptide mimotope of the disclosure with a biological sample and detecting the presence of antibodies that bind to the peptide mimotope on the substrate; or (b) contacting a sample with a labeled peptide mimotope of the disclosure and detecting a complex comprising an antibody bound to the labeled peptide; wherein antibodies that bind to the peptide mimotope are indicative of a subject having antibodies to oxLDL adducts. Further secondary antibodies to the IgG or IgM epitopes can then be used to determine the amount of IgG and/or IgM antibodies bound by the peptide mimotopes. For example, anti-IgG and anti-IgM antibodies can be labeled and used to detect the IgG and IgM. Such anti-IgG and IgM antibodies are known (e.g., goat anti-human IgM or IgG linked to horseradish peroxidase (Cappell-Durham, N.C.)).

An exemplary biochemical test for identifying IgG and/or IgM autoantibodies to OSEs employs a standardized test format, such as the Enzyme Linked Immunosorbent Assay or ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). It is understood that commercial assay enzyme-linked immunosorbant assay (ELISA) kits for various plasma constituents are available.

In another embodiment, the level of OxPL/apoB, IgG and/or IgM autoantibodies to OSEs is further correlated with, the age of the subject at the time the values are measured, the subject's gender, and/or the subject's race.

In another embodiment, an article of manufacture is provided. The article may include packaging material containing biomolecules that interact with apoB, OxPL, IgG or IgM autoantibodies to OSEs. The packaging material may include a label or package insert indicating that the biomolecules can be used for calculating a risk level based upon the values of OxPL/apoB, IgG and/or IgM in sample compared to normal standard samples of risk and non-risk values.

In yet another embodiment, an array is provided. The array may include a substrate having a plurality of addresses, each address having disposed thereon a set of one or more biomolecules that specifically interact with apoB; OxPL; or IgG or IgM autoantibodies to OSEs.

The methods of the disclosure can be used with an array (i.e., "biochip" or "microarray") that includes immobilized biomolecules that facilitate the detection of a particular molecule or molecules in a biological sample. Biomolecules that identify the biomarkers described above can be included in a custom array for detecting IgG or IgM autoantibodies to OSEs. The array can also include biomolecules that identify additional factors indicative of the efficacy of a treatment for CAD, stroke, TIA and/or PAD. Additional biomolecules can be included in a custom array of the disclosure.

The term "array," as used herein, generally refers to a predetermined spatial arrangement of binding islands, biomolecules, or spatial arrangements of binding islands or biomolecules. Arrays according to the disclosure that include biomolecules immobilized on a surface may also be referred to as "biomolecule arrays." Arrays according to the disclosure that comprise surfaces activated, adapted, prepared, or modified to facilitate the binding of biomolecules to the surface may also be referred to as "binding arrays." The disclosure also contemplates surfaces bearing multiple arrays, referred to as "multiple arrays" or "repeating arrays." The use of the term "array" herein may encompass biomolecule arrays, binding arrays, multiple arrays, and any combination thereof, the appropriate meaning will be apparent from context. The biological sample can include fluid or solid samples from any tissue of the body including plasma.

An array of the disclosure or a solid phase comprises a substrate. By "substrate" or "solid support" or other grammatical equivalents, herein is meant any material appropriate for the attachment of biomolecules and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TEFLON®, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins or agarose. Such coatings can facilitate the use of the array with a biological sample derived from serum.

A planar array of the disclosure will generally contain addressable locations (e.g., "pads", "addresses," or "microlocations") of biomolecules in an array format. The size of the array will depend on the composition and end use of the array. Arrays containing from about 2 different biomolecules to many thousands can be made. In some embodiments, the compositions of the disclosure may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates. Parallel microfluidic devices comprising arrays would be useful for parallel measurements of OxPL and total ApoA content of a biological sample.

As an alternative to planar arrays, bead based assays in combination with flow cytometry have been developed to perform multiparametric immunoassays. In bead based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay.

Product formation of the biomarker with their immobilized capture biomolecules can be detected with fluorescence based reporter systems. Biomarkers can either be labeled directly by a fluorogen or detected by a second fluorescently labeled capture biomolecule. The signal intensities derived from captured biomarkers are measured in a flow cytometer. The flow cytometer first identifies each microsphere by its individual color code. Second the amount of captured biomarkers on each individual bead is measured by the second color fluorescence specific for the bound target. This allows multiplexed quantitation of multiple targets from a single sample within the same experiment. Sensitivity, reliability and accuracy are compared to standard microtiter ELISA procedures. With bead based immunoassay systems serum components can be simultaneously quantified from biological samples. An advantage of bead-based systems is the individual coupling of the capture biomolecule to distinct microspheres.

An array of the disclosure encompasses any means for detecting a biomarker molecule such as, for example, IgG or IgM autoantibodies to OSEs and OxPL/apoB levels. For example, microarrays can be biochips that provide high-density immobilized arrays of recognition molecules (e.g., OSEs or peptide mimotopes), where biomarker binding is monitored indirectly (e.g., via fluorescence). In addition, an array can be of a format that involves the capture of proteins by biochemical or intermolecular interaction, coupled with direct detection by mass spectrometry (MS).

Arrays and microarrays that can be used with the new methods to detect the biomarkers described herein can be made according to the methods described in U.S. Pat. Nos. 6,329,209; 6,365,418; 6,406,921; 6,475,808; and 6,475,809, and U.S. patent application Ser. No. 10/884,269, which are incorporated herein in their entirety. New arrays, to detect specific selections of sets of biomarkers described herein can also be made using the methods described in these patents.

Surfaces useful according to the disclosure may be of any desired shape (form) and size. Non-limiting examples of surfaces include chips, continuous surfaces, curved surfaces, flexible surfaces, films, plates, sheets, tubes, and the like. Surfaces have areas ranging from approximately a square micron to approximately 500 $cm^2$. The area, length, and width of surfaces according to the disclosure may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces and then placed into wells. In certain embodiments, such as where a surface without wells is used, binding islands may be formed or biomolecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

Modifications or binding of biomolecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," Drug Discovery Today 4(8):363-369 (1999), and references cited therein; Lakowicz J R, Principles of Fluorescence Spectroscopy, 2nd Edition, Plenum Press (1999).

In another embodiment, a pre-packaged diagnostic kit for determining whether a therapy is effective for treating coronary artery disease is provided. The kit may include an array as described above, instructions for using the array, and instructions for calculating risk based upon the level of OxPL on apoB, IgG or IgM autoantibodies to OSEs in a test sample when compared to standardized samples.

Arrays of the disclosure suitable for identifying coronary artery disease, stroke risk, TIA risk, PAD risk and/or CVD, and the efficacy of a treatment therefore, may be included in kits. Such kits may also include, as non-limiting examples, reagents useful for preparing biomolecules for immobilization onto binding islands or areas of an array, reagents useful for detecting modifications to immobilized biomolecules, or reagents useful for detecting binding of biomolecules from solutions of interest to immobilized biomolecules, and instructions for use. Likewise, arrays comprising immobilized biomolecules may be included in kits. Such kits may also include, as non-limiting examples, reagents useful for detecting modifications to immobilized biomolecules or for detecting binding of biomolecules from solutions of interest to immobilized biomolecules.

In other embodiments, a method for identifying plaque regression, reverse cholesterol transport or stabilization in a blood vessel in a subject, is provided. The method includes obtaining a first sample comprising plasma from a subject; administering a therapy to the subject; obtaining a second sample from the subject following administration of the therapy; determining the level of IgG or IgM autoantibodies to OSEs in the first sample and second sample and comparing the change in values to standardized values indicative of risk of CVD, stroke and/or TIA. The information may be provided to a caregiver in various means including directly, paper printout over, computer screen or over the internet to a remote location.

As discussed above, the level of OxPL/apoB in the samples obtained from the subject are determined. For example, the levels can be measured with two or more different biomolecules. The first biomolecule specifically interacts with OxPL and the second biomolecule specifically interacts with, e.g., apoB-100. The antibody that interacts with OxPL may be, for example, E06 or DLH3. In one embodiment, a substrate is coated with a binding agent that binds apoB (e.g., an antibody), a sample is contacted with the substrate comprising the binding agent, washed and a secondary antibody that binds OxPLs is then contacted with the substrate comprising bound apoB. The amount of bound OxPL can then be determined. The bound OxPL antibodies will be associated with OxPL bound to apoB, thereby providing the amount of OxPL on apoB. In one embodiment, the disclosure relates to a method for measuring the plasma content of oxidized phospholipids on apolipoprotein B particles (OxPL/apoB). For example, the content of OxPL and apoB may be measured with monoclonal antibodies that are specific for each of these OxPL constituents.

In yet another embodiment, a method for determining the phospholipid content of an apoB particle, is provided. The method includes obtaining a sample comprising apoB; determining the level of oxidized phospholipid (OxPL) in the sample; determining the level of apoB in the sample; and calculating an index by determining the ratio of the OxPL level to the apoB level. The method also includes measuring the amount of IgM and/or IgG antibodies to OxPL present in the sample. For example, an increasing or increased (e.g., compared to a prior data point) of IgM is indicative of a subject that has a reduced risk of stroke or ischemic events.

The methods and compositions of the disclosure also provide a method of optimizing the treatment of a subject having or at risk of having a stroke, cardiovascular disease or disorder. The disclosure provides an approach to treating such a disorder by integrating diagnostics and therapeutics to improve the real-time treatment of a subject having, for example, a stroke, cardiovascular disease or disorder associated with cholesterol, HDL, or LDL content. For example, multiparameter immunoassays specific for a series of diagnostically relevant molecules such as IgG or IgM autoantibodies to OSEs; OxPL; apoA; or apoB can be used to follow the progress of a subject undergoing treatment. The markers provided herein are particularly adaptable for use in diagnosis and treatment because they are available in easily obtained body fluids such as blood or serum.

In one embodiment, the assay format comprises the capture of IgG or IgM autoantibodies to OSEs. OSEs or mimotopes of the disclosure can be used in the assay. The binding agent (e.g., the mimotope) can be linked to a solid phase or support (e.g., a bead, tissue culture plate, glass slide or the like. The agent is bound to the solid phase either by adsorption thereon or by covalent attachment.

In one embodiment, the solid phase is coated with an antigens recognized by IgG or IgM autoantibodies to OSEs (or other binding agent, e.g., peptide mimotopes of the disclosure that interacts with IgG or IgM autoantibodies to OSEs), such that the IgG or IgM autoantibodies to OSEs are separated from a sample, such as for example, bodily fluids, tissue or cells, by allowing the IgG or IgM autoantibodies to OSEs to be bound thereto. The specimen may be any biological material containing antibodies to OSEs, such as plasma or lymphatic fluid, or it may be the fluid portion of cells, such as those of the liver. The sample may be the crude specimen, or it may be a separated fraction, for example, a protein enriched sample. The optimum time necessary for IgG or IgM autoantibodies to OSEs to bind quantitatively to the support can be determined empirically, by sequential trials.

After the IgG or IgM autoantibodies to OSEs are bound to the support, unbound IgG or IgM antibodies are removed by rinsing with a buffer solution. Sites of the support which are available to non-specific binding may be blocked by treatment with a solution containing a protein such as for example albumin or gelatin.

To determine the amount of IgG and/or IgM in a sample a secondary antibody that specifically binds to the IgG or IgM is added to the solid support/phase and allowed to incubate for a period of time sufficient to allow the secondary antibody to interact with an antigenic site on the IgG or IgM antibody bound to the solid substrate/phase. The secondary antibody may be detectably labeled such that suitable quantitation of the autoantibody may be determined. Suitable labels include fluorescent labels, luminescent labels, radioactive labels, chromogenic labels and the like. Unbound antibody can then be removed from the sample by washing.

A sample run in parallel can be performed or from the same biological sample to measure the presence of OxPL on bound apolipoprotein B. OxPL can be determined by using an antibody that interacts with the oxidized phospholipid. Such antibodies are known in the art and includes the antibody designated E06. Additional antibodies have been described in the literature that can also bind OxPL, such as DLH3 (Itabe et al., *J Lipid Res.* 1996; 37:45-53).

The label attached to the probing antibodies may be an enzyme, such as peroxidase, alkaline phosphatase, or beta-galactosidase, as are commonly used in ELISA assays. These enzymes react with appropriate substrates to produce a colored compound, the concentration of which can be measured by its absorbance. In one embodiment of the test, however, the interaction of alkaline phosphatase or beta-galactosidase with a substrate methylumbelliferonyl phosphate generates a fluorescent product, detected by the same automated system used to measure the Nile Red binding.

Chemiluminescent enzyme-linked immunosorbent assay can be used also in apolipoprotein quantification. When the tagging enzyme is peroxidase, the detection system is Luminol/$H_2O_2$ (Stevens, P. et al., Lab Res. Methods Biol. Med. 4:205 (1980)). The amount of light produced in these reactions is quantified using appropriate light measuring devices such as ML 1000 microplate luminometer (Dynatech Lab, Inc., 14340 Sully Field Circle, Chantilly, Va. 22021). Typically, when either fluorescent or chemiluminescent signals are to be read, the test is carried out on black plates.

In other embodiments, the disclosure provides databases and computerized methods of analyzing and storing data associated with treatment regimens for atherosclerosis related diseases. A database generated by the methods and analyses described herein can be included in, or associated with, a computer system for determining whether a treatment is successful. The database can include a plurality of digitally encoded "reference" (or "control") profiles. Each reference profile of the plurality can have a plurality of values, each value representing a level of, for example, IgG or IgM autoantibodies to OSEs detected in blood or serum of an individual having, or predisposed to having, an atherosclerosis or stroke related disorder. Alternatively, a reference profile can be derived from an individual who is normal. Both types of profiles can be included in the database for consecutive or simultaneous comparison to a subject profile. The computer system can include a server containing a computer-executable code for receiving a profile and identifying from the database a matching reference profile that is diagnostically relevant to the subject profile. The identified profile can be supplied to a caregiver for diagnosis or further analysis.

Using standard programs, electronic medical records (EMR) can be accumulated to provide a database that combines, for example, index data with additional information such as the age of a patient or any other parameter useful for predicting whether or not a subject will or is responding to a treatment. Patient information can be randomly assigned a numerical identifier to maintain anonymity with testing laboratories and for security purposes. All data can be stored on a network that provides access to multiple users from various geographic locations.

Thus, the various techniques, methods, and aspects of the disclosure described herein can be implemented in part or in whole using computer-based systems and methods. Additionally, computer-based systems and methods can be used to augment or enhance the functionality described herein, increase the speed at which the functions can be performed, and provide additional features and aspects as a part of, or in addition to, those of the invention described herein.

Antibodies capable of interacting with apoB or OxPL are known in the art. For example, a monoclonal antibody, designated E06 has been described that binds specifically to the phosphorylcholine head group of oxidized but not native phospholipids. Accordingly, this antibody can be used to determine the level of oxidized phospholipids in complex with apoB molecules. This antibody can be adapted for use in any immunoassay. For example, chemiluminsecent ELISA assays are described elsewhere herein. Additional antibodies have been described in the literature that can also bind OxPL, such as DLH3 (Itabe et al., J Lipid Res. 1996; 37:45-53).

As discussed herein, "OxPL/apoB" is a measure of the content of oxidized phospholipids (OxPL) per apoB-100 particle. Also as discussed herein, "apoB-IC", or "IC/apoB", refers to the total amount of apoB in circulating LDL immune complexes. Collectively, the OxPL/apoB and IC/ApoB measurements are used to specifically quantify the content of OxPL and IC, respectfully, on each captured apoB particle.

Accordingly, the disclosure relates to the measurement of IgG or IgM autoantibodies to OSEs and may further include measuring OxPL/apoB with or without simultaneous measurement of IC/apoB levels and/or total OxPL/apoB and total IC/apoB as indices of stroke risk or atherogenesis.

The invention is illustrated in the following examples, which are provided by way of illustration and are not intended to be limiting.

EXAMPLES

Example 1

Study Subjects.

The Bruneck Study is a prospective population-based survey of the epidemiology and pathogenesis of atherosclerosis with sex- and age-stratified random sample of all inhabitants of Bruneck, Italy (125 women and 125 men in the 5th to 8th decades each, n=1000). The current study focuses on the 1995 examination and the follow-up period for clinical events between 1995 and 2010 (100% follow-up). The appropriate ethics committees approved the study protocol and all study subjects gave their written informed consent before entering the study. All risk factors were assessed by validated standard procedures. Study methodology and laboratory methods for factors listed in Table 1 were previously described in detail (Kiechl S et al., Arterioscler Thromb Vasc Biol 1999; 19:1484-90; Tsimikas S et al., J Am Coll Cardiol 2006; 47:2219-28; and Kiechl S et al., Arterioscler Thromb Vasc Biol 1999; 19:1491-8).

Determination of OSE on Lipoproteins.

Oxidized phospholipids on apolipoprotein B-100 (OxPL/apoB) levels and IgG and IgM autoantibodies to malondialdehyde-modified (MDA-LDL) and copper-oxidized (Cu-Ox-LDL) and apoB-immune complexes (apoB-IC) were measured in 765 subjects from the 1995 study point and in 656 subjects from the 2000 timepoint. OxPL/apoB levels were measured as previously described by chemiluminescent ELISA using the murine monoclonal antibody E06, which binds to the phosphocholine (PC) head group of oxidized but not native phospholipids (Tsimikas, et al.). When the OxPL/apoB levels in Bruneck were first published, they were reported in 2 ways: as relative light units (RLU) and as a ratio of E06 (OxPL RLU) binding to presence of apoB on the plate, measured by monoclonal antibody MB47 (apoB RLU), i.e. OxPL/apoB ratio. It has been demonstrated that these measurements provide nearly identical results and are essentially interchangeable, thus future studies have reported OxPL/apoB as RLU due to the more simple methodology of their determination. In the current analysis, both levels are shown but the analyses are based on OxPL/apoB RLU data. IgG and IgM autoantibodies and (apoB-IC) and Lp(a) were measured as previously described (Mayr et al., Journal of the American College of Cardiology 2006; 47:2436-43; Tsimikas et al., J Lipid Res 2007; 48:425-33; and Kronenberg et al., Circulation 1999; 100:1154-60). The intra and inter-assay coefficients of variation for OxPL/apoB were 6-10%.

Assessment of Future Cardiovascular Events.

The primary composite cardiovascular endpoint included ischemic stroke, myocardial infarction, new-onset unstable angina, acute coronary interventions and vascular death (due to ischemic stroke, myocardial infarction, sudden cardiac death or aortic aneurysm rupture). The extended composite cardiovascular endpoint additionally included transient ischemic attacks (TIAs) and all revascularization procedures. Acute coronary artery disease included myocardial infarction (fatal and non-fatal), new-onset unstable angina, acute coronary interventions and sudden cardiac deaths. Myocardial infarction was deemed confirmed when World Health Organization criteria for definite disease status were met. Stroke and TIA were classified according to the criteria of the National Survey of Stroke. All other revascularization procedures (angioplasty and surgery) were carefully recorded. Ascertainment of events or procedures did not rely on hospital discharge codes or the patient's self-report but on a careful review of medical records provided by the general practitioners and files of the Bruneck Hospital and the extensive clinical and laboratory examinations performed as part of the study protocols. Cases were ascertained from 1995 through 2010, and one hundred percent follow-up was achieved.

Statistics.

Calculations were performed with SPSS 18.0 and Stata 12.0 MP software packages. Continuous variables were presented as means±SD or medians (interquartile range), and dichotomous variables as percentages. Differences in baseline levels of vascular risk attributes between subjects with and without subsequent CVD (1995 to 2010) were analysed with the Student's t-test and $X^2$-test. Variables with a skewed distribution were $\log_e$-transformed to satisfy the assumption of normality and constant variance of the residuals. To quantify the within-person variability of OSE biomarkers, regression dilution ratios (RDRs) were calculated based on 656 repeated measurements in samples taken 5 years apart (1995 and 2000). Long-term average levels of these markers were estimated by means of multivariate regression calibration. Cox proportional hazard models were used to assess whether baseline OSE biomarker levels were independent predictors of CVD risk. For this purpose, OSE biomarkers were either entered as continuous variables or categorized in thirds (tertiles). One model was used and adjusted for age, sex, and previous cardiovascular disease and one that additionally included systolic blood pressure, smoking, diabetes, ferritin level, LDL and HDL cholesterol, alcohol consumption, social status, sports activity (Baecke score), and $\log_e$-transformed levels of C-reactive protein ('multivariable Cox model'). As exposure, a third model included predicted long-term average levels instead of baseline levels of OSE biomarkers. ApoB and Lp(a) were not included because of the high correlation with LDL-C and OxPL/apoB, respectively, and the potential problem of collinearity. Results remained virtually the same when apoB was used instead of LDL-C or when Lp(a) was used instead of OxPL/apoB. To test for linear trend, the median level was used in each tertile group of OxPL/apoB as a continuous variable. All analyses were repeated using Lp(a) concentration instead of OxPL/apoB level. Proportional hazard assumptions were tested for OxPL/apoB and Lp(a) and were satisfied in all models. Differential associations in subgroups were analysed by inclusion of appropriate interaction terms. All reported P values are two-sided.

Baseline Characteristics.

Table 1 displays the baseline characteristics of study subjects (n=765) according to incident cardiovascular disease during follow-up (1995-2010). Subjects developing the primary CVD endpoint (n=138) were more likely to be older and male, have higher levels of LDL-C, vascular, coagulation, inflammatory and anthropomorphic and activity risk factors, and to have pre-existent CVD at study entry in 1995.

TABLE 1

Baseline characteristics of study subjects (n = 765) according to incident cardiovascular disease during follow-up (1995-2010).

| | Primary composite CVD endpoint | | |
|---|---|---|---|
| Variable | No (n = 627) Mean ± SD, Median (IQR)* or % | Yes (n = 138) Mean ± SD, Median (IQR)* or % | P value |
| Demographic parameters | | | |
| Age, years | 61.4 ± 10.9 | 68.8 ± 10.5 | <0.0001 |
| Female sex, % | 51.5% | 40.6% | 0.020 |
| Oxidation-specific biomarkers | | | |
| OxPL/apoB, ratio | 0.098 ± 0.109 | 0.161 ± 0.172 | <0.0001 |
| OxPL/apoB, RLU | 9094 ± 9966 | 14773 ± 15590 | <0.0001 |
| Lp-PLA$_2$ activity, μmol/min/L | 768.8 ± 195.2 | 858.6 ± 201.1 | <0.0001 |
| MDA-LDL IgM, RLU | 17504 ± 9739 | 16271 ± 7956 | 0.165 |
| Cu-OxLDL IgM, RLU | 4848 ± 3854 | 4227 ± 2493 | 0.018 |
| ApoB-IC IgM, RLU | 5159 ± 2826 | 4544 ± 2255 | 0.006 |
| MDA-LDL IgG, RLU | 17642 ± 10713 | 18109 ± 11886 | 0.650 |
| Cu-OxLDL IgG, RLU | 9577 ± 6284 | 10769 ± 11017 | 0.086 |
| ApoB-IC IgG, RLU | 7033 ± 3871 | 6787 ± 3419 | 0.491 |

TABLE 1-continued

Baseline characteristics of study subjects (n = 765) according to incident cardiovascular disease during follow-up (1995-2010).

| | Primary composite CVD endpoint | | |
|---|---|---|---|
| Variable | No (n = 627) Mean ± SD, Median (IQR)* or % | Yes (n = 138) Mean ± SD, Median (IQR)* or % | P value |
| Triglycerides, mg/dL | 109 (78-15) | 119 (93-170) | 0.010 |
| HDL cholesterol, mg/dL | 59.5 ± 16.2 | 56.4 ± 17.3 | 0.049 |
| LDL cholesterol, mg/dL | 143.3 ± 37.1 | 153.1 ± 40.5 | 0.006 |
| Lipoprotein(a), mg/dL | 10.8 (4.5-31.0) | 21.5 (7.0-55.4) | 0.001 |
| Apolipoprotein A, mg/dL | 166.5 ± 27.1 | 163.8 ± 29.9 | 0.296 |
| Apolipoprotein B, mg/dL | 113.6 ± 30.2 | 125.4 ± 34.5 | <0.0001 |
| Vascular risk factors | | | |
| Hypertension, % | 66.0% | 75.4% | 0.034 |
| Systolic BP, mmHg | 146.6 ± 19.8 | 154.3 ± 22.4 | <0.0001 |
| Diastolic BP, mmHg | 86.7 ± 8.9 | 88.0 ± 9.7 | 0.118 |
| Current smoking, % | 20.4% | 17.4% | 0.420 |
| Smoking, cigarettes/d | 2.6 ± 6.2 | 2.6 ± 6.5 | 0.992 |
| Diabetes (ADA), % | 6.9% | 13.8% | 0.007 |
| Fasting glucose, mg/dL | 100.8 ± 22.7 | 109.5 ± 32.8 | 0.004 |
| Ferritin, μg/L | 131.3 ± 153.7 | 151.8 ± 162.8 | 0.162 |
| Uric acid, mg/dL | 4.6 ± 1.3 | 5.2 ± 1.3 | <0.0001 |
| Urinary albumin, g/L | 9.0 (7.0-16.0) | 12.0 (8.8-54.8) | <0.0001 |
| Fibrinogen, mg/dL | 284.8 ± 72.9 | 303.6 ± 70.5 | 0.006 |
| C-reactive protein, mg/L | 1.5 (0.8-3.0) | 2.1 (1.1-4.5) | 0.010 |
| Physical activity and body composition | | | |
| Sports index (Baecke), score | 2.4 ± 0.9 | 2.2 ± 0.8 | 0.002 |
| Alcohol, g/day | 24.2 ± 31.4 | 22.9 ± 30.1 | 0.640 |
| Body-mass index, kg/m$^2$ | 25.5 ± 3.8 | 26.1 ± 4.1 | 0.088 |
| Waist-hip ratio, cm/cm | 0.93 ± 0.07 | 0.95 ± 0.07 | 0.001 |
| Pre-existent CVD | | | |
| CVD, % | 6.9% | 25.4% | <0.0001 |

To convert values for cholesterol to mmol/L, multiply by 0.02586. To convert values for triglycerides to mmol/L, multiply by 0.01129.
BP denotes blood pressure; CVD, cardiovascular disease; ADA, American Diabetes association.
RLU = relative light units
*Median and interquartile range (IQR) is presented for markedly skewed variables.

OxPL/apoB levels and Lp-PLA$_2$ activity levels were higher in patients with incident CVD. In contrast, IgM antibodies to MDA-LDL and Cu-OxLDL, and apoB-IC were lower in subjects with CVD events, with the latter two associations achieving significance. IgG Cu-OxLDL antibodies trended to be higher in patients with subsequent CVD. Within-person variability of these markers was generally low. The regression dilution ratio of measurements taken 5 years apart was 0.83 (0.80-0.86) for OxPL/apoB levels, 0.91 (0.81, 1.01) for IgG and 0.72 (0.64-0.79) for IgM Cu-OxLDL, 0.70 (0.64-0.76) for IgG and 0.87 (0.82-0.91) for IgM MDA-LDL, and 0.67 (0.61-0.74) for IgG and 0.69 (0.62-0.76) for IgM ApoB-IC.

OxPL/apoB and Incident CVD.

The risk of the primary composite CVD endpoint increased across tertiles of OxPL/apoB and was particularly prominent in tertile 3 (Table 2). These associations were consistent across 3 models of multivariable adjustment: 1) following adjustment for age, sex and prior CVD; 2) in a multivariable Cox model of 13 clinical variables including high sensitivity C-reactive protein (hsCRP); and 3) in the same Cox model with "usual" OxPL/apoB levels that considers the variability of OxPL/apoB over time estimated by multivariate regression calibration based on measurements in 1995 and 2000. In model 3, the highest tertile of OxPL/apoB was associated with a hazard ratio (HR) and 95% confidence interval (95% CI) of 2.4 (1.5-3.7, p<0.001), compared to the lowest tertile. Similar findings were present for the extended CVD endpoint that additionally included TIA and all revascularization procedures (Table 2). For individual endpoints, OxPL/apoB was a strong predictor of stroke [HR 3.6 (1.8-7.4), p<0.001] and combined stroke/TIA [HR 3.2 (1.7-6.1), p<0.001]. These findings were consistent when the data was evaluated as continuous variables per 1-standard deviation (SD) in OxPL/apoB (Tables 2 and 3), showing HR of approximately 1.25-1.5. In this analysis, OxPL/apoB also predicted vascular death (Table 2).

TABLE 2

ASSOCIATION OF OXPL/APOB TERTILE GROUPS WITH CARDIOVASCULAR DISEASE RISK IN THE BRUNECK STUDY COHORT (1995-2010) (N = 765).

| Model | Hazard ratio (95% CI) OxPL/apoB tertile groups | | | P value for trend | Hazard ratio (95% CI) per 1-SD unit increase in OxPL/apoB | P value |
|---|---|---|---|---|---|---|
| | I | II | III | | | |
| **Primary composite CVD endpoint* (n = 138)** | | | | | | |
| Adjusted for age, sex and prior CVD | 1.0 | 1.1 (0.7-1.7) | 2.1 (1.4-3.1) | <0.0001 | | <0.0001 |
| Multivariable Cox model† | 1.0 | 1.1 (0.7-1.7) | 2.2 (1.5-3.4) | <0.0001 | | <0.0001 |
| Multivariable Cox model†‡ | 1.0 | 1.2 (0.7-1.9) | 2.4 (1.5-3.7) | <0.0001 | | <0.0001 |
| Extended composite CVD endpoint* (n = 154) | | | | | | |
| Adjusted for age, sex and prior CVD | 1.0 | 1.0 (0.6-1.6) | 2.1 (1.4-3.0) | <0.0001 | | <0.0001 |
| Multivariable Cox model† | 1.0 | 1.0 (0.6-1.5) | 2.1 (1.4-3.1) | <0.0001 | | <0.0001 |
| Multivariable Cox model†‡ | 1.0 | 1.1 (0.7-1.8) | 2.2 (1.4-3.4) | <0.0001 | | <0.0001 |
| Stroke (n = 60) | | | | | | |
| Adjusted for age, sex and prior CVD | 1.0 | 1.1 (0.5-2.4) | 2.9 (1.5-5.4) | <0.001 | | <0.001 |
| Multivariable Cox model† | 1.0 | 1.0 (0.5-2.2) | 3.2 (1.6-6.2) | <0.0001 | | <0.001 |
| Multivariable Cox model†‡ | 1.0 | 1.5 (0.7-3.4) | 3.6 (1.8-7.4) | <0.0001 | | <0.001 |
| Stroke/TIA (n = 76) | | | | | | |
| Adjusted for age, sex and prior CVD | 1.0 | 1.1 (0.6-2.2) | 2.8 (1.6-4.9) | <0.0001 | | 0.001 |
| Multivariable Cox model† | 1.0 | 1.1 (0.5-2.1) | 2.9 (1.6-5.1) | <0.0001 | | 0.002 |
| Multivariable Cox model†‡ | 1.0 | 1.5 (0.8-3.1) | 3.2 (1.7-6.1) | <0.0001 | | 0.002 |
| Acute coronary artery disease* (n = 70) | | | | | | |
| Adjusted for age, sex and prior CVD | 1.0 | 1.2 (0.6-2.1) | 1.5 (0.9-2.7) | 0.148 | | 0.032 |
| Multivariable Cox model† | 1.0 | 1.2 (0.7-2.3) | 1.5 (0.8-2.7) | 0.190 | | 0.066 |
| Multivariable Cox model†‡ | 1.0 | 1.1 (0.6-2.2) | 1.5 (0.8-2.9) | 0.139 | | 0.066 |
| Myocardial infarction (n = 53) | | | | | | |
| Adjusted for age, sex and prior CVD | 1.0 | 1.2 (0.6-2.3) | 1.3 (0.7-2.5) | 0.546 | | 0.134 |
| Multivariable Cox model† | 1.0 | 1.2 (0.6-2.4) | 1.2 (0.6-2.4) | 0.662 | | 0.244 |
| Multivariable Cox model†‡ | 1.0 | 1.0 (0.5-2.2) | 1.2 (0.6-2.5) | 0.525 | | 0.244 |
| Vascular death* (n = 64) | | | | | | |
| Adjusted for age, sex and prior CVD | 1.0 | 0.9 (0.5-1.8) | 1.3 (0.7-2.4) | 0.244 | | 0.031 |
| Multivariable Cox model† | 1.0 | 0.9 (0.5-1.7) | 1.3 (0.7-2.4) | 0.216 | | 0.048 |
| Multivariable Cox model†‡ | 1.0 | 0.8 (0.4-1.7) | 1.2 (0.6-2.3) | 0.381 | | 0.048 |
| Death from all causes (n = 250) | | | | | | |
| Adjusted for age, sex and prior CVD | 1.0 | 1.1 (0.8-1.5) | 1.0 (0.8-1.4) | 0.985 | | 0.977 |
| Multivariable Cox model† | 1.0 | 0.9 (0.7-1.3) | 1.2 (0.9-1.6) | 0.157 | | 0.264 |
| Multivariable Cox model†‡ | 1.0 | 1.3 (0.9-1.8) | 1.4 (1.0-1.9) | 0.176 | | 0.264 |

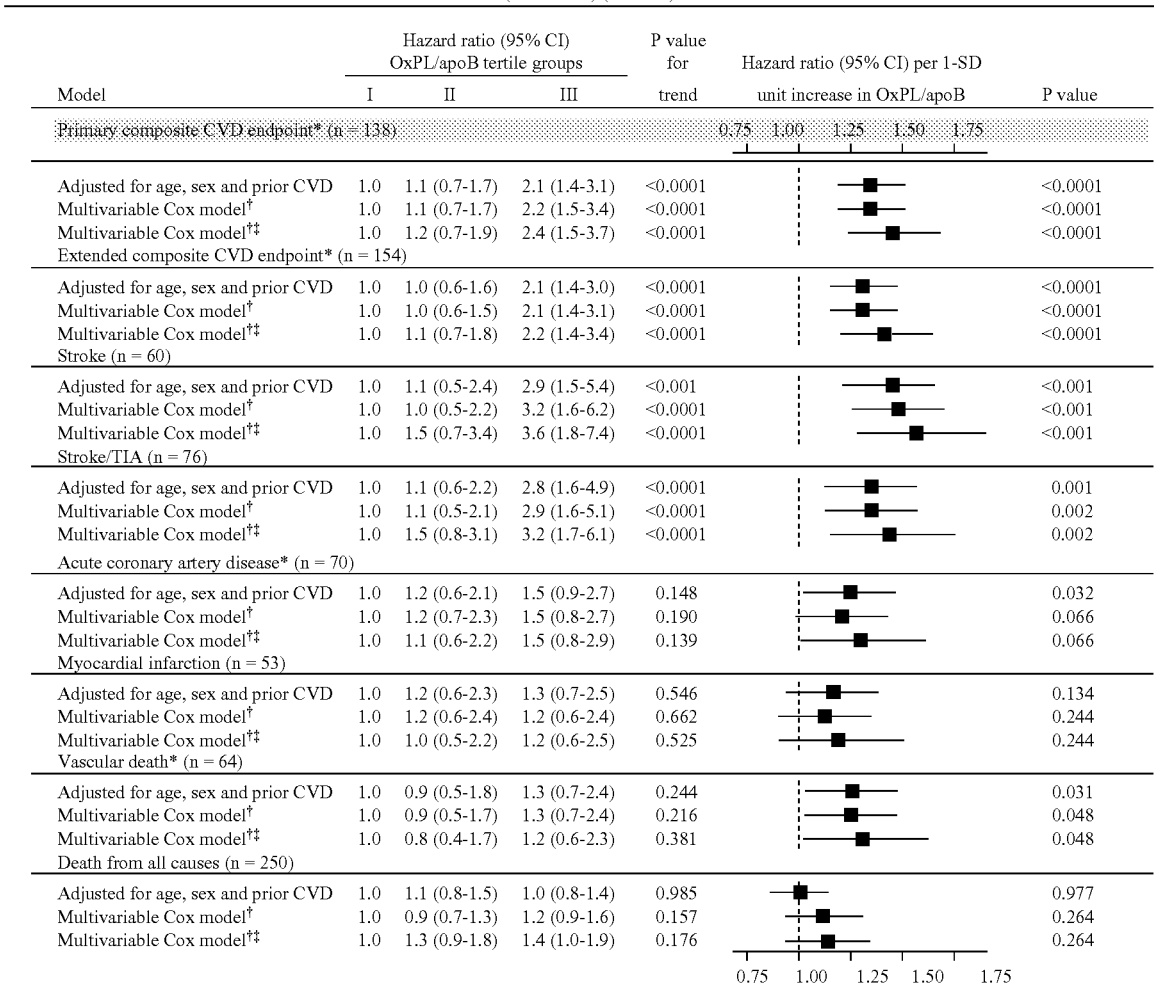

Squares and lines are hazard ratios (HRs) and 95% confidence intervals. HRs were derived from Cox models and calculated for OxPL tertile groups (left-hand columns) and for a 1-SD unit increase in OxPL level (right-hand columns). In all analysis, only the first outcome event occurring in study participants was considered while potential further or recurrent events were censored.
*The primary composite cardiovascular endpoint subsumes ischemic stroke, acute coronary artery disease and vascular death. The extended composite cardiovascular endpoint additionally considers TIAs and all revascularization procedures. Acute coronary artery disease subsumes myocardial infarction (fatal and non-fatal), new-onset unstable angina, acute coronary interventions and sudden cardiac deaths. Vascular deaths subsume deaths due to ischemic stroke, myocardial infarction, sudden cardiac death and aortic aneurysm rupture.
†Multivariable adjustment: age, sex, previous cardiovascular disease, systolic blood pressure, smoking, diabetes, ferritin level, LDL and HDL cholesterol, alcohol consumption, social status, sports activity (Baecke score), and log$_e$-transformed levels of C-reactive protein.
‡"Usual" OxPL levels were used instead of baseline levels. "Usual" OxPL level considers the variability of OxPL over time and was estimated by multivariate regression calibration.

TABLE 3

ASSOCIATION OF OXIDATION-SPECIFIC BIOMARKERS WITH CARDIOVASCULAR DISEASE RISK IN THE BRUNECK STUDY COHORT (1995-2010) (N = 765).

| | Primary composite CVD endpoint (n = 138) | | Stroke (n = 60) | | Acute coronary artery disease (n = 70) | |
|---|---|---|---|---|---|---|
| | HR (95% CI) HR (95% CI)* HR (95% CI)† | P value P value* | HR (95% CI) HR (95% CI)* HR (95% CI)† | P value P value* P value† | HR (95% CI) HR (95% CI)* HR (95% CI)† | P value P value* |
| OxPL/apoB | 1.34 (1.19-1.51) | <0.0001 | 1.42 (1.19-1.69) | 0.0001 | 1.22 (1.01-1.46) | 0.036 |
| | 1.37 (1.20-1.56) | <0.0001 | 1.47 (1.21-1.78) | <0.0001 | 1.20 (0.99-1.45) | 0.066 |

TABLE 3-continued

ASSOCIATION OF OXIDATION-SPECIFIC BIOMARKERS WITH CARDIOVASCULAR
DISEASE RISK IN THE BRUNECK STUDY COHORT (1995-2010) (N = 765).

|  | Primary composite CVD endpoint (n = 138) | | Stroke (n = 60) | | Acute coronary artery disease (n = 70) | |
|---|---|---|---|---|---|---|
|  | HR (95% CI)<br>HR (95% CI)*<br>HR (95% CI)† | P value<br>P value* | HR (95% CI)<br>HR (95% CI)*<br>HR (95% CI)† | P value<br>P value*<br>P value† | HR (95% CI)<br>HR (95% CI)*<br>HR (95% CI)† | P value<br>P value* |
|  | 1.38 (1.21-1.57) | <0.0001 | 1.48 (1.22-1.80) | <0.0001 | 1.21 (1.00-1.46) | 0.052 |
| Cu-OxLDL IgG | 1.11 (0.98-1.27) | 0.104 | 1.25 (1.07-1.46) | 0.005 | 0.91 (0.69-1.21) | 0.516 |
|  | 1.18 (1.03-1.37) | 0.022 | 1.33 (1.12-1.58) | 0.001 | 0.95 (0.71-1.28) | 0.738 |
|  | 1.18 (1.02-1.37) | 0.028 | 1.32 (1.11-1.58) | 0.002 | 0.94 (0.70-1.27) | 0.703 |
| MDA-LDL IgM | 0.72 (0.53-0.98) | 0.034 | 0.81 (0.63-1.05) | 0.109 | 0.82 (0.69-0.97) | 0.019 |
|  | 0.69 (0.50-0.95) | 0.021 | 0.79 (0.61-1.02) | 0.075 | 0.79 (0.66-0.95) | 0.011 |
|  | 0.69 (0.50-0.94) | 0.018 | 0.79 (0.61-1.03) | 0.084 | 0.79 (0.66-0.95) | 0.010 |

Hazard ratios (HRs) and 95% confidence intervals were derived from Cox models and calculated for a 1-SD unit increase in OxPL level, Cu-OxLDL IgG and MDA-LDL IgM antibodies. Cox models included age, sex, prior CVD, OxPL/apoB level, Cu-OxLDL IgG and MDA-LDL IgM antibodies.
*HRs (95% CI) and P values in bold are from multivariable Cox models with additional adjustment for systolic blood pressure, smoking, diabetes, ferritin level, LDL and HDL cholesterol, alcohol consumption, social status, sports activity (Baecke score), and $log_e$-transformed level of C-reactive protein.
†"Usual" OxPL/apoB level was used instead of baseline OxPL/apoB levels. "Usual" OxPL/apoB level considers the variability of OxPL/apoB over time and was estimated by multivariate regression calibration.

Cumulative hazard plots depicting the composite CVD endpoint (FIG. 1A) and stroke (FIG. 1B) indicate a progressive divergence in event frequency over 15-year follow-up in OxPL/apoB tertile 3 compared to tertiles 1 and 2.

Figure 2:
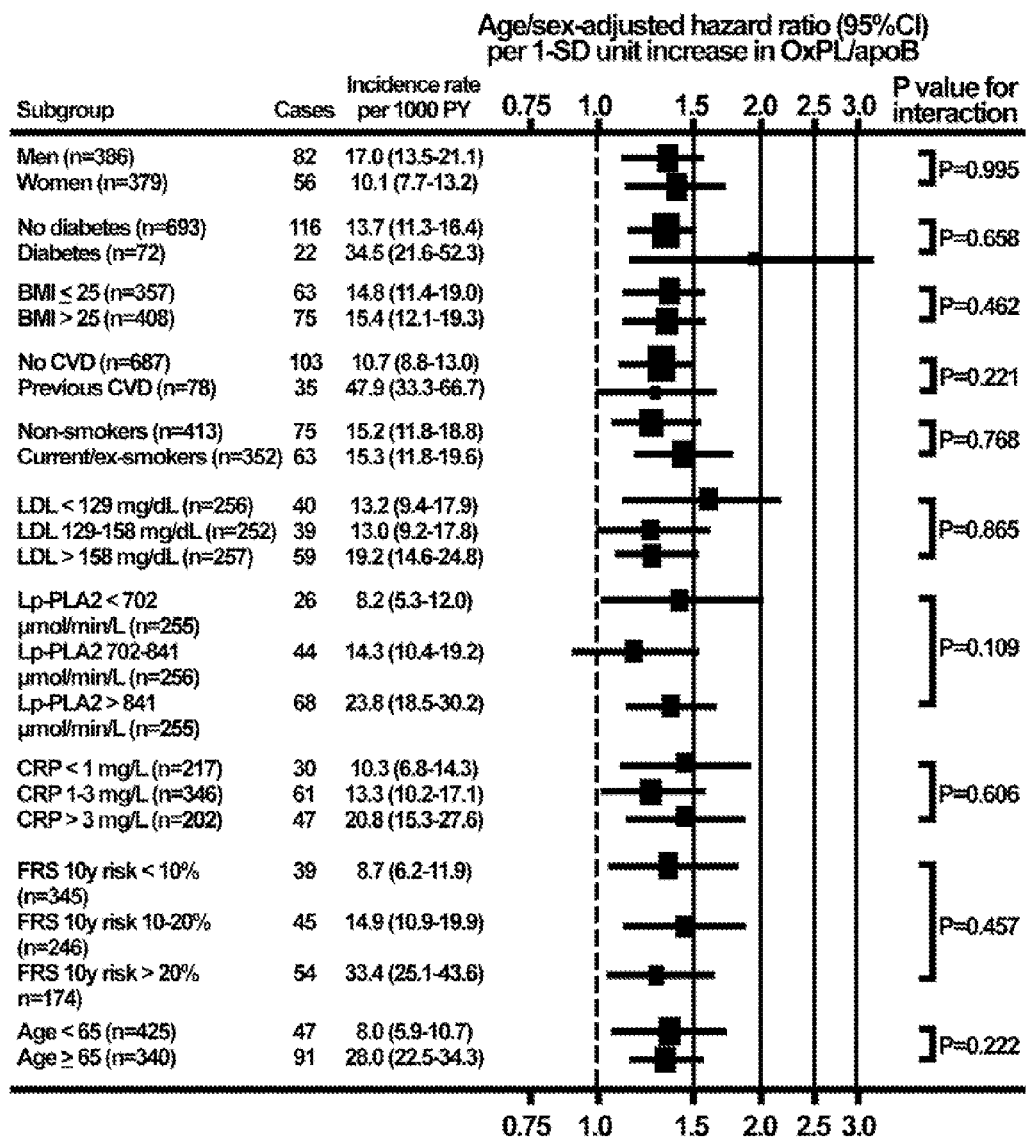
FIG. 2 shows the association between OxPL/apoB and incident cardiovascular disease (primary composite endpoint) in various subgroups (Bruneck Study, 1995-2010, n=765). Abbreviation: PY, person years; CVD, cardiovascular disease; Lp-$PLA_2$, lipoprotein-associated phospholipase $A_2$ activity; CRP, high sensitivity C-reactive protein; FRS, Framingham Risk Score. Squares and lines are hazard ratios and 95% confidence intervals (95% CIs) calculated for a 1-SD unit increase in OxPL/apoB ratio. The size of squares reflects the number of individuals in each subgroup. All models were adjusted for age, sex, previous cardiovascular disease, systolic blood pressure, smoking, diabetes, ferritin level, LDL and HDL cholesterol, alcohol consumption, social status, sports activity (Baecke score), and $\log_e$-transformed levels of CRP. Interactions were calculated by inclusion of appropriate interaction terms.
Figure 3:
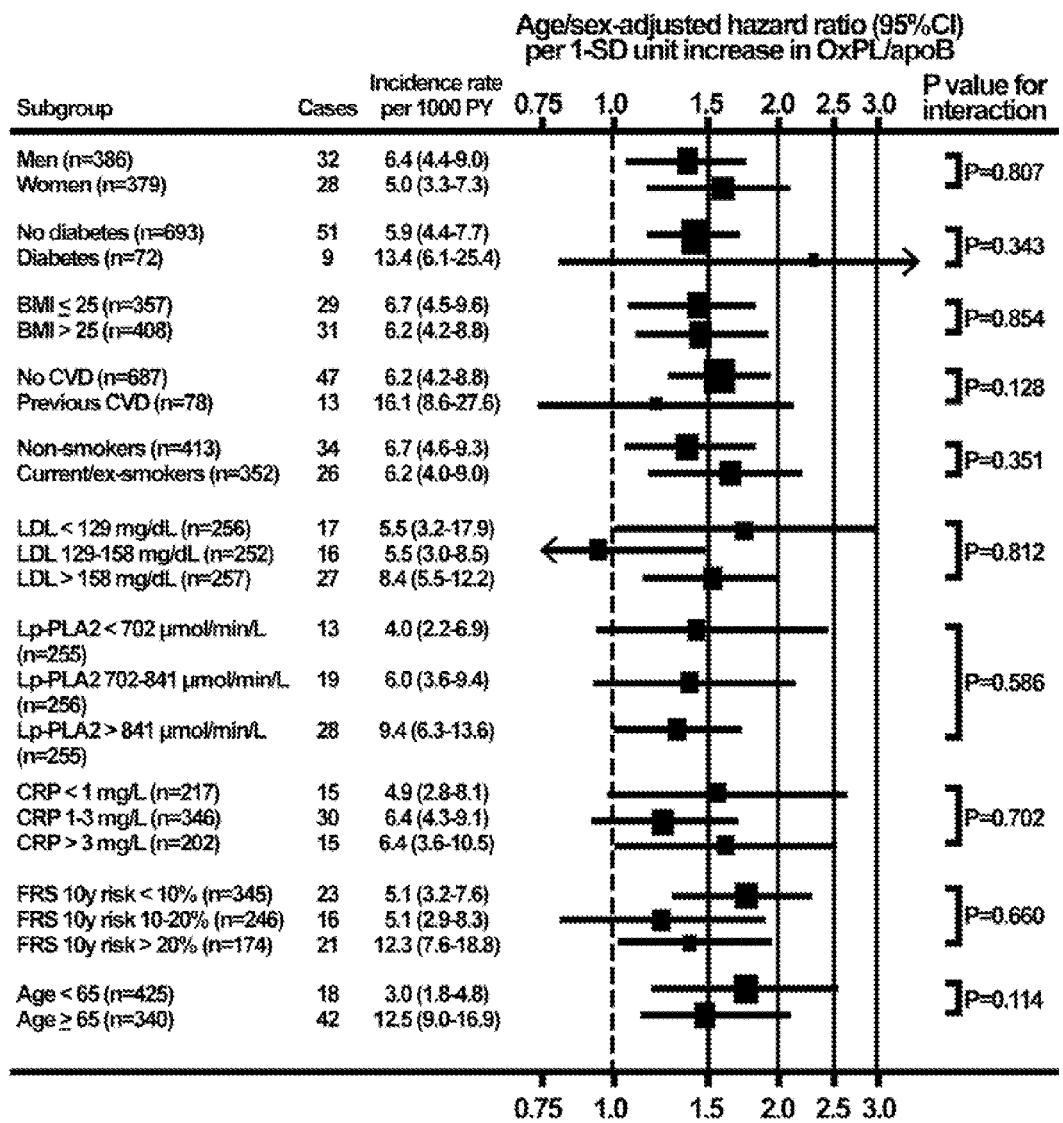
FIG. 3 shows the association between OxPL/apoB and incident stroke in various subgroups (Bruneck Study, 1995-2010, n=765). Abbreviation: PY, person years; CVD, cardiovascular disease; Lp-PLA2, lipoprotein-associated phospholipase $A_2$ activity; CRP, high sensitivity C-reactive protein; FRS, Framingham Risk Score. Squares and lines are hazard ratios and 95% confidence intervals (95% CIs) calculated for a 1-SD unit increase in OxPL/apoB. The size of squares reflects the number of individuals in each subgroup. All models were adjusted for age, sex, previous cardiovascular disease, systolic blood pressure, smoking, diabetes, ferritin level, fibrinogen level, LDL and HDL cholesterol, waist-to-hip ratio, alcohol consumption, social status, Lp-$PLA_2$ activity, sports activity (Baecke score), uric acid level, fasting glucose, and loge-transformed levels of CRP and urinary albumin. Interactions were calculated by inclusion of appropriate interaction terms.

Subgroup analysis revealed consistent findings across sex, age, CVD risk factors, Lp-PLA$_2$ activity, hsCRP and Framingham Risk Score (FRS) for both the tertile analysis and as continous variables for 1-SD change for the primary composite CVD endpoint (FIG. 2) and for stroke as an individual endpont (FIG. 3).

IgG and IgM Autoantibodies and apoB-IC and Incident CVD.

In a next step a model was fitted with consideration of both OxPL/opaB and autoantibodies to OSE. In Model 3, IgG Cu-OxLDL were associated with higher risk of the composite endpoint (HR (95% CI) 1.18 (1.02-1.37, p=0.028 for 1-SD unit increase) and the individual endpoint of stroke (HR (95% CI) 1.32 (1.02-1.37, p=0.002) (Table 3). In contrast, in model 3, IgM MDA-LDL [HR 0.79 (0.66-0.95), p=0.010] was associated with lower risk of composite CVD, as well as stroke. If IgM MDA-LDL was replaced by IgM Cu-OxLDL the repective HR amounted at 0.78 (0.61-0.98), (p=0.037). IgG and IgM apoB-IC were not predictive of events in the multivariable models.

Receiver Operating Classification Curves and Reclassification.

Figure 4:
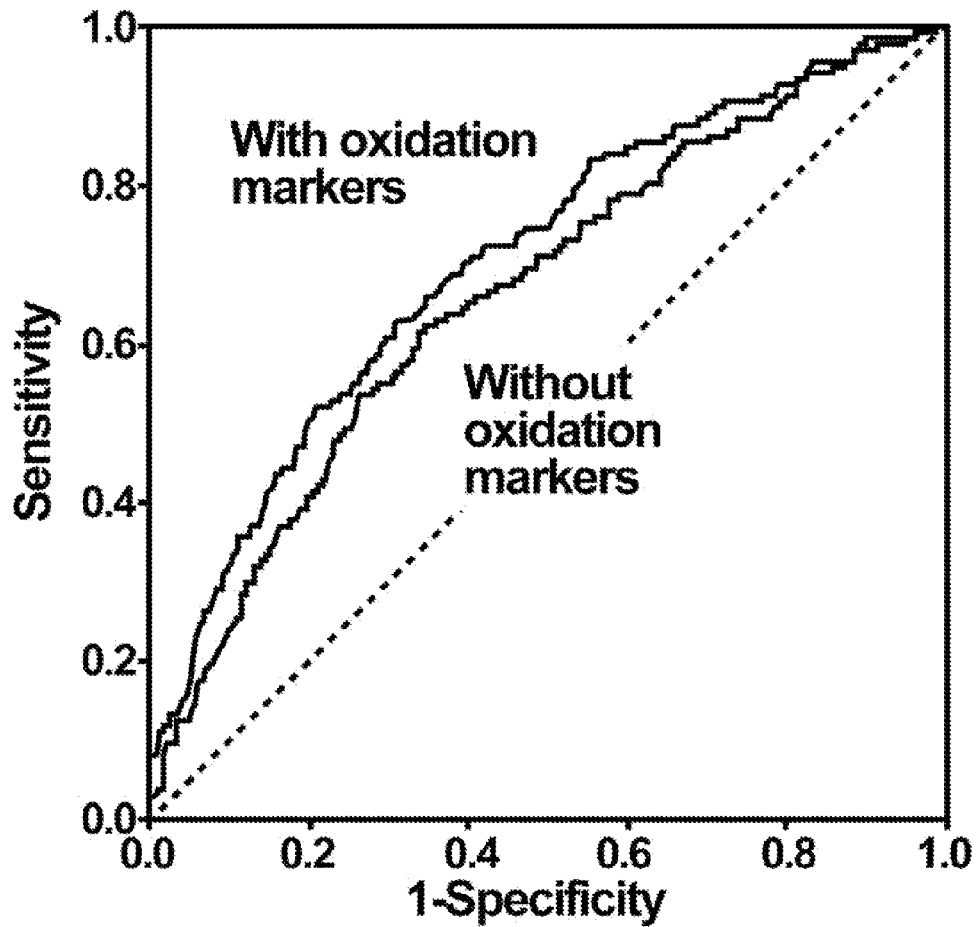
FIG. 4 shows receiver Operating Classification Curves for the CVD endpoint with inclusion of the oxidation markers (OxPL/apoB, Cu-OxLDL IgG and MDA IgM) in the area under the curve (AUC). The reference comparison was Framingham Risk Score (FRS) without oxidation biomarkers included.

Receiver Operating Classification Curves (ROC) for the primary endpoint were determined (FIG. 4). With inclusion of the oxidation markers (OxPL/apoB, Cu-OxLDL IgG and MDA IgM) the area under the curve (AUC) increased from 0.664 [0.629-0.697] (Framingham Risk Score (FRS) only) to 0.705 [0.672-0.737]. This change, although modest [A AUC 0.042 [0.001-0.083] p=0.048], is statistically significant. The net reclassification index NRI is 0.163 (two-sided p=0.0044). In subjects with incident CVD (n=138) 35 were correctly reclassified to a higher risk category and 18 were reclassified to a lower category, in subjects who remain free of CVD (n=627) 108 are correctly reclassified to a lower risk category and 83 were reclassified to a higher category (Categories: 10-year FRS risk <10%, 10-20%, >20%). In subjects at intermediate risk (10-20% 10-year risk) (n=305) the NRI was 0.332 (p<0.0001) (Table 4).

TABLE 4

Risk reclassification based on oxidation markers (OxPL/apoB, Cu-OxLDL IgG and MDA IgM) in patients who experienced a cardiovascular disease endpoint (n = 138) and in those who remained free of cardiovascular disease during follow-up (n = 627; 1995-2010).

|  | Model based on the Framingham risk score only<br>Model additionally considering oxidation markers | | | |
|---|---|---|---|---|
| Frequency (n) | | | | |
| Risk categories<br>(10-year cardio-<br>vascular disease risk) | <10<br>percent<br>risk | 10-20<br>percent<br>risk | >20<br>percent<br>risk | Total |
| People who remained free of cardiovascular disease (n = 627) | | | | |
| <10 percent risk | 291 | 49 | 9 | 349 |
| 10-20 percent risk | 92 | 119 | 25 | 236 |
| >20 percent risk | 1 | 15 | 26 | 42 |
| Total | 384 | 183 | 60 | 627 |
| People who experienced a cardiovascular disease endpoint (n = 138) | | | | |
| <10 percent risk | 28 | 13 | 4 | 45 |
| 10-20 percent risk | 15 | 36 | 18 | 69 |
| >20 percent risk | 0 | 3 | 21 | 24 |
| Total | 43 | 52 | 43 | 138 |

This reclassification table compares a model based on the Framingham risk score only with a model considering the Framingham risk score, and levels of oxidation markers (OxPL/apoB, Cu-OxLDL IgG and MDA IgM).

Example 2

Study Population

The HPFS (Health Professionals Follow-up Study) is a prospective cohort study of 51,529 male dentists, optometrists, pharmacists, podiatrists, osteopathic physicians, and veterinarians 40 to 75 years of age that began in 1986. The NHS study (Nurses' Health Study) is a prospective cohort study of 121,700 female nurses 30 to 55 years of age that began in 1976. From individuals in these 2 studies, 18,224 men provided blood specimens in 1994, and 32,826 women provided a blood sample in 1989. Individuals were excluded who had a history of cardiovascular disease (CVD), including: MI; surgical/percutaneous revascularization of the coronary, carotid, or peripheral beds; confirmed PAD; stroke; and transient ischemic attack.

The case-control analytic datasets include 143 incident cases and 429 control subjects in the HPFS study and 144 incident cases and 432 control subjects in the NHS study. Cases were matched 1:3 to control subjects on age, race (NHS study only), month of blood draw (within 3 months), fasting status, and smoking history (never/former/current). Control subjects were selected at random, conditional on the matching factors, from participants free of PAD at the time the case occurred (risk set sampling). Because older age categories had fewer participants, the age match range was relaxed year-by-year if necessary to a maximum of within 3 years.

Assessment of OxPL, Lp(a), Autoantibodies, and Immune Complexes.

Blood samples were shipped overnight with a cold pack to the central laboratory, centrifuged on arrival, aliquoted, and stored in liquid nitrogen at −130° C. to 196° C. The HPFS specimens were anticoagulated with ethylenediaminetetraacetic acid, and NHS specimens were anticoagulated with heparin, and 95% of HPFS bloods and 97% of NHS bloods were received within 24 h. A validated plasma assay was used to measure OxPL/apoB, with the murine monoclonal antibody E06 that recognizes the phosphocholine (PC) group on oxidized but not on native phospholipids. E06 similarly recognizes the PC covalently bound to bovine serum albumin (BSA), as in PC-BSA. A 1:50 dilution of plasma in phosphate-buffered saline is added to microtiter wells coated with monoclonal antibody MB47, which binds a saturating amount of apoB-100 to each well. Finally, biotinylated E06 is used to determine OxPL/apoB in relative light units (RLU). Within-person 5-year reproducibility of frozen samples is high (r=0.78), and pilot-tests showed that OxPL/apoB levels are stable over 24 h on ice (intra-class correlation coefficient=0.96).

To facilitate comparison of absolute OxPL/apoB levels across studies, the reporting of OxPL/apoB levels as nanomolar (nmol/1 or nM) OxPL was used rather than RLU OxPL with a novel standard curve of PC equivalents. The standard curve is generated by plating known concentrations of phosphocholine-modified bovine serum albumin (PC-BSA), which has approximately 16 mole of PC/mole of BSA (Biotech Technologies, Novato, Calif.), and is recognized by E06. Biotin-E06 is then added to detect the number of moles of PC in the linear range on the plate and is measured in RLU. This standard curve is then used to convert the RLU derived from wells containing individual human samples to OxPL equivalents. This method is reported as nanomoles of PC found on OxPL/1 plasma (i.e., nanomolar or nM) for each sample. Because each mole of OxPL has 1 PC headgroup recognized by E06, this can be reported as nM OxPL.

The Lp(a) levels were determined with a chemiluminescent enzyme-linked immunoadsorbent assay with MB47-coated wells, a 1:400 plasma dilution, and biotinylated monoclonal antibody LPA4. Chemiluminescent enzyme-linked immunoadsorbent assay was used to measure IgG and IgM autoantibodies to MDA-LDL and apoB-immune complexes (ApoB-IC). Measured coefficients of variation in duplicate samples were 8% for OxPL/apoB, 13% for Lp(a), 11% for IgG autoantibodies, 9% for IgM autoantibodies, 10% for IgG ApoB-IC, and 10% for IgM ApoB-IC in the HPFS study. Coefficients of variation were 21% for OxPL/apoB, 13% for Lp(a), 9% for IgG autoantibodies, 7% for IgM autoantibodies, 16% for IgG ApoB-IC, and 25% for IgM ApoB-IC in the NHS study.

Assessment of PAD.

Participants reported the occurrence of professionally diagnosed medical conditions, including claudication and revascularization for arterial disease of the leg, during the previous 2 years on biennial mailed questionnaires. Medical records were collected from treating physicians and hospitals for those who reported either condition. Professionals blinded to biomarker status reviewed and confirmed PAD diagnoses with medical records.

PAD was defined as arterial disease below the aortic bifurcation (i.e., excluding abdominal aortic aneurysm and renal artery stenosis). Confirmed PAD required at least 1 of the following (in order of severity/certainty): 1) report of amputation, bypass, or other revascularization procedure (e.g., angioplasty) for occlusive artery disease; 2) angiogram showing at least 50% stenosis of at least 1 artery with congruent symptoms in the ipsilateral limb; 3) ankle-brachial index (ABI)=0.9; or 4) diagnosis of physician confirmed by medical record review.

Assessment of Covariates.

Questionnaires provided information about medical history and lifestyle habits, including detailed information about smoking, medication use, weight, parental history of MI, alcohol, physical activity, diet, and post-menopausal hormone use. Participants reported the average amount of time they spent/week on various activities such as walking, jogging, running, bicycling, and tennis. This information was used to calculate weekly energy expenditure in metabolic equivalent taskhours. Body mass index (BMI) was calculated by dividing weight (kg) by squared height ($m^2$). Both physical activity and BMI measures are highly valid.

A laboratory certified by the National Heart, Lung and Blood Institute/Centers for Disease Control and Prevention Lipid Standardization Program analyzed all other biochemical markers by means of commercially available analytic systems. The laboratory measured high-density lipoprotein cholesterol and triglycerides enzymatically and LDL cholesterol by a homogenous direct method from Roche Diagnostics (Indianapolis, Ind.). An immunoturbidimetric assay on the Roche P Modular system from Roche Diagnostics quantified the concentration of high-sensitivity C-reactive protein, with reagents and calibrators from DiaSorin (Stillwater, Minn.). The Roche P Modular system uses turbidimetric immunoinhibition and hemolyzed whole blood or packed red cells to determine hemoglobin A1c (Roche Diagnostics, Indianapolis, Ind.).

Statistical Analysis.

Generalized linear mixed models and Cochran-Mantel-Haenszel tests were used to compare continuous variables and categorical variables by case/control status, respectively, accounting for clustering by matching status. The shape of the associations of OxPL/apoB, Lp(a), autoantibodies, and ApoB-IC with PAD risk were analyzed with cubic splines, adjusting for all covariates. Conditional logistic regression, conditioning on matching factors, was used to estimate odds ratios for PAD according to level of OxPL/apoB and present estimates adjusted for matching factors and additionally for other PAD risk factors. Because risk set sampling was employed, these odds ratios are reported as unbiased estimates of the incidence rate ratio (RR).

Covariates were included in the models as linear variables if appropriate or as categorical variables if discrete or their association with PAD was nonlinear. Multicollinearity was examined among covariates with variance inflation factors. Because the test for heterogeneity was not statistically significant, a meta-analysis was used with fixed effects to pool the RR estimates for OxPL/apoB and Lp(a). Effect modification was tested by including interaction terms between OxPL/apoB and the potential effect modifier (continuous variable) in the models and pooled the interaction terms for men and women with a meta-analysis with fixed effects. The levels of autoantibodies and ApoB-IC were analyzed in similar fashion. All analyses used SAS statistical software (version 9.2, Cary, N.C.).

Among men, medical reports of amputation, bypass, or other revascularization procedure confirmed 87 PAD cases (61%), angiogram or Doppler ultrasound confirmed 15 cases (10%), ABI <0.9 confirmed 23 cases (16%), and physician diagnosis confirmed 18 cases (13%). Among women, surgery or procedure confirmed 74 cases (51%), angiogram confirmed 24 cases (17%), ABI confirmed 39 cases (27%), and physician diagnosis confirmed 7 cases (5%). Compared with control subjects, PAD cases had higher levels of traditional CVD risk factors (Table 5). Although cases and control subjects were matched on current smoking status, cases still had a significantly higher average number of pack-years compared with control subjects.

TABLE 5

Baseline Characteristic of Cases and Match Control Subjects

|  | Women | | | Men | | |
|---|---|---|---|---|---|---|
|  | Cases (n = 144) | Control Subjects (n = 432) | p Value* | Cases (n = 143) | Control Subjects (n = 429) | p Value* |
| Age (yrs) | 59.9 ± 5.2 | 60.0 ± 5.2 | Matched | 65.4 ± 8.1 | 65.3 ± 8.1 | Matched |
| Oxidation-related factors | | | | | | |
| OxPL/apoB (nM) | 8.46 (3.9-19.3) | 5.00 (2.9-10.6) | <0.001 | 15.24 (12.4-23.6) | 14.15 (12.3-19.4) | 0.02 |
| OxPL/apoB (RLU) | 4.882 (2.237-11.135) | 2.887 (1.649-6.132) | <0.001 | 8.800 (7.162-1.3601) | 8.173 (7.126-11.184) | 0.02 |
| Lipoprotein (a) (mg/dl) | 35.1 (8.7-72.3) | 13.1 (4.9-43.1) | <0.001 | 7.6 (2.8-34.3) | 4.5 (1.6-17.7) | 0.007 |
| IgG AA to MDA-LDL (RLU) | 8.776 (6.394-12.669) | 8.541 (5.572-12.758) | 0.34 | 2.313 (1.411-4.949) | 2.733 (1.741-4.350) | 0.36 |
| IgM AA to MDA-LDL (RLU) | 20.457 (14.001-26.529) | 18.966 (13.903-25.145) | 0.22 | 9.684 (5.836-14.986) | 9.213 (6.363-13.823) | 0.16 |
| IgG ApoB-IC (RLU) | 1.106 (862-1.439) | 1.076 (791-1.494) | 0.94 | 1.620 (562-1.600) | 1748 (1.376-2.374) | 0.22 |
| IgM ApoB-IC (RLU) | 1.490 (897-2.574) | 1478 (960-2.393) | 0.17 | 885 (562-1.600) | 921 (601-1.425) | 0.29 |
| Lipids | | | | | | |
| Triglycerides (mg/dl) | 110 (85-161) | 106 (73-145) | 0.34 | 143 (105-195) | 115 (80-165) | 0.001 |
| HDL-C (mg/dl) | 60.5 ± 19.9 | 62.1 ± 17.1 | 0.42 | 41.7 ± 11 | 48.5 ± 14 | <0.001 |
| LDL-C (mg/dl) | 60.5 ± 44 | 142 ± 38 | 0.16 | 139 ± 35 | 131 ± 33 | 0.02 |
| hsCRP (mg/dl) | 2.56 (1.25-4.70) | 1.62 (0.73-3.33) | 0.07 | 2.24 (1.2-3.5) | 1.16 (0.5-2.3) | 0.005 |
| HbA$_{1c}$ (%) | 5.46 (5.28-5.72) | 5.33 (5.16-5.56) | <0.001 | 5.56 (5.3-6.0) | 5.41 (5.2-5.6) | <0.001 |
| Smoking status | | | | | | |
| Never | 30 (21%) | 90 (21%) | Matched | 23 (18%) | 62 (20%) | Matched |
| Past | 56 (39%) | 170 (39%) | Matched | 78 (60%) | 242 (59%) | Matched |
| Current | 58 (40%) | 172 (40%) | Matched | 32 (22%) | 90 (21%) | Matched |
| 1-14 cigarettes/day | 18 (13%) | 86 (20%) | | 15 (11%) | 44 (11%) | |
| 15-34 cigarettes/day | 31 (22%) | 80 (19%) | | 11 (8%) | 33 (8%) | |
| 35+ cigarettes/day | 9 (6%) | 5 (1%) | | 4 (3%) | 9 (2%) | |
| Packs-yrs (yrs) | 32.3 ± 25.6 | 22.0 ± 21.3 | <0.001 | 28.7 ± 24 | 22.5 ± 22 | <0.001 |
| Physical activity (MET h/wk) | 12.8 (4.7-24.9) | 13.6 (5.0-28.1) | 0.69 | 22.7 (8.0-43.8) | 27.4 (10.3-52.8) | 0.003 |
| History of hypertension | 68 (47%) | 137 (32%) | <0.001 | 70 (49%) | 130 (30%) | <0.001 |
| History of diabetes | 19 (13%) | 12 (3%) | <0.001 | 28 (20%) | 16 (4%) | <0.001 |
| History of hyper-cholesterolemia | 84 (58%) | 200 (46%) | 0.01 | 82 (57%) | 167 (44%) | 0.005 |
| Alcohol | | | | | | |
| Never drinker | 49 (34%) | 130 (30%) | | 35 (24%) | 84 (20%) | |
| Former drinker | 44 (31%) | 137 (32%) | | 24 (17%) | 80 (19%) | |
| <1 drink/day | 29 (20%) | 109 (25%) | 0.43 | 39 (27%) | 123 (29%) | 0.81 |
| 1-1.9 drinks/day | 12 (8%) | 20 (5%) | | 23 (16%) | 65 (15%) | |
| 2+ drinks/day | 9 (6%) | 31 (7%) | | 22 (15%) | 76 (18%) | |
| Parental history of MI <age 60 yrs | 31 (22%) | 61 (14%) | 0.03 | 22 (15%) | 44 (10%) | 0.09 |
| BMI category | | | | | | |
| <25 | 84 (56%) | 259 (60%) | | 62 (43%) | 204 (48%) | |
| 25-29.9 | 38 (26%) | 132 (31%) | 0.13 | 67 (47%) | 196 (46%) | 0.42 |
| 30+ | 22 (15%) | 41 (9%) | | 14 (10%) | 29 (7%) | |
| Aspirin use | 29 (20%) | 89 (21%) | 0.91 | 80 (56%) | 164 (43%) | 0.01 |
| Post-menopausal | 131 (95%) | 390 (95%) | 0.72 | | | |
| Ever used post-menopausal hormones† | 96 (72%) | 257 (63%) | 0.04 | | | |
| Currently using post-menopausal hormones | 57 (43%) | 183 (45%) | 0.84 | | | |

Values are mean ± DS, median (interquartile range), or B (%).

*Generalized linear mixed models for continuous variables amd Cochran-Mantel-Haenszel test for categorical variables (to account for matching/correlation between control subjects); matching criteria were age, month of blood draw, tasting status, and smoking status.
†Among post-menopausal women.
AA to MDA-LDL = autoantibodies to malondaidehyde-modified low-density lipoprotein cholesterol;
ApoB-IC = apollpoprotein B-100 immune complexes;
BMI = body mass index;
hsCRP = high sensitivity C-reactive protein;

TABLE 5-continued

Baseline Characteristic of Cases and Match Control Subjects

| | Women | | | Men | | |
|---|---|---|---|---|---|---|
| | Cases (n = 144) | Control Subjects (n = 432) | p Value* | Cases (n = 143) | Control Subjects (n = 429) | p Value* |

$HbA_{1c}$ = hemoglobin $A_{1c}$;
HDL-C = high-density lipoprotein cholesterol;
Ig = immunoglobulin;
LDL-C = low-density lipoprotein cholesterol;
MET h = metabolic equivalent task-hours;
MI = myocardial infarction;
OxPL/apoB = oxidized phospholipids on apollpoprotein B-100-containing lipoproteins;
RLU = relative light units.

OxPL/apoB and Lp(a).

Women had considerably lower levels of OxPL/apoB compared with men, whereas the distribution of Lp(a) overlapped substantially across sexes, with somewhat greater levels among women. OxPL/apoB was not strongly correlated with standard CVD risk factors.

Figure 5:
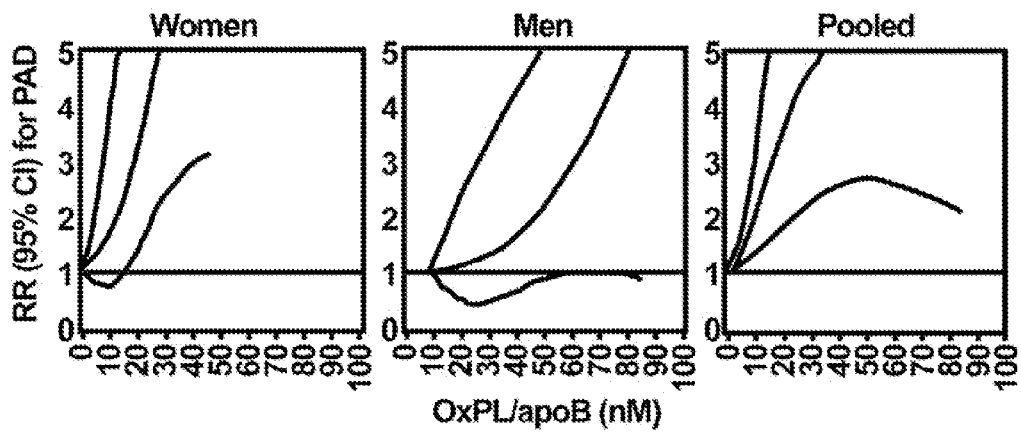
FIG. 5 shows the adjusted relationship between plasma levels of OxPL/apoB and RR of PAD. Data derive from a cubic spline conditional logistic regression model with age, race (women only), smoking status, fasting status, and date of blood sampling as matching variables. The model is adjusted for triglycerides, high-density lipoprotein cholesterol, low-density lipoprotein cholesterol, high-sensitivity C-reactive protein, hemoglobin Alc, history of diabetes, history of hypertension, pack-years of smoking, parental history of myocardial infarction before age 60, aspirin use, body mass index, physical activity, post-menopausal hormone use (women only), and sex (pooled only). The 95% confidence interval (CI) is indicated by the dashed lines. ApoB=apolipoprotein B-100-containing lipoproteins; OxPL=oxidized phospholipids; PAD=peripheral artery disease; RR=relative risk.
Figure 6:
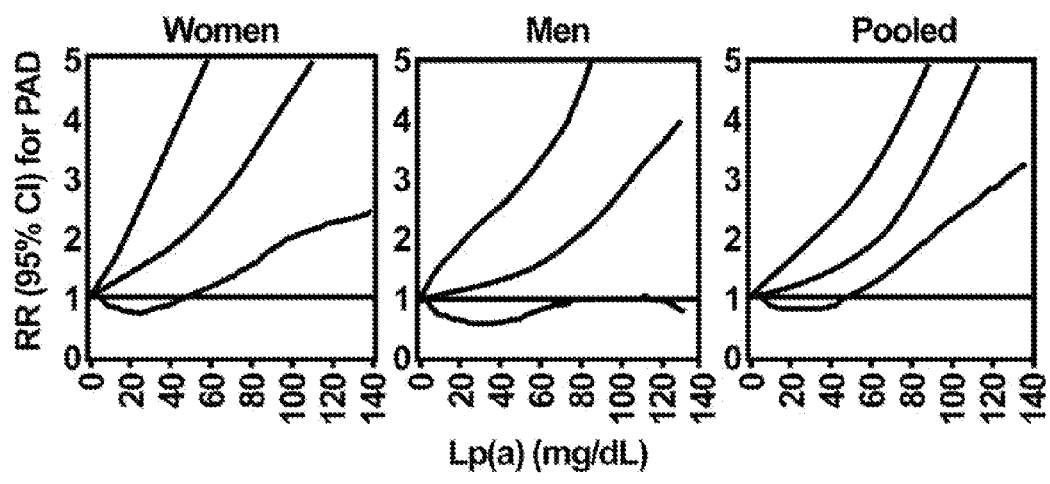
FIG. 6 shows adjusted relationship between plasma levels of Lp(a) and RR of PAD.
Figure 7:
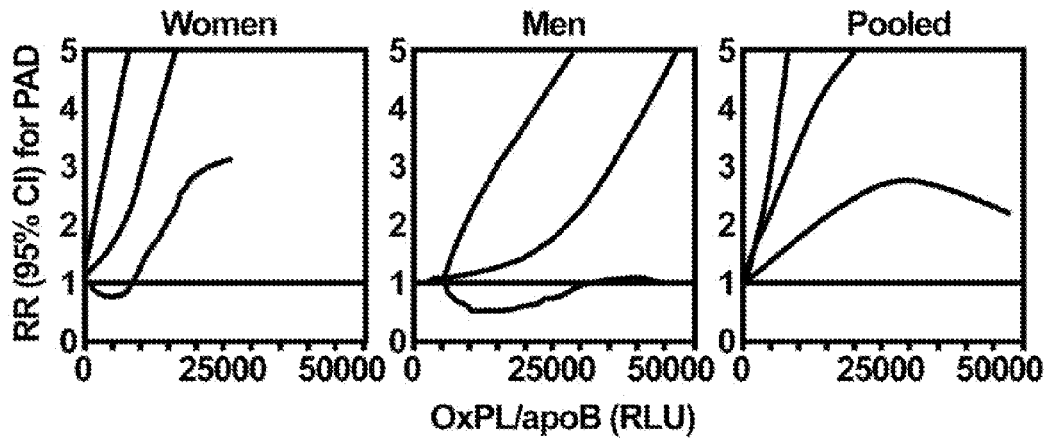
FIG. 7 shows adjusted relationship between plasma levels of OxPL/apoB (RLU) and RR or PAD.

The association between OxPL/apoB and Lp(a) and risk of PAD appeared linear (FIGS. 5 to 7), and likelihood ratio tests for nonlinearity were not statistically significant (p>0.05), comparing a model with the linear term with a model with the linear and cubic spline terms. Therefore the results are presented with units of 1 SD of nM OxPL/apoB. The results are additionally presented with RLU, because previous work used OxPL/apoB measured in RLU. There was a 51% (95% confidence interval [CI]: 24% to 85%) increase in risk of PAD for each 1-SD increase in OxPL/apoB in women and a 23% (95% CI: 0% to 52%) increase in men in full multivariable models (Table 6). These estimates were essentially the same for matching adjusted models (53% in women, and 24% in men). Similarly, there was a 52% (95% CI: 24% to 87%) increase in risk of PAD for each 1-SD increase in Lp(a) in women, and a 24% (95% CI: 0% to 53%) increase in men in full multivariable models (Table 7).

Because statistically significant heterogeneity was not observed between the NHS and HPFS studies, the results were pooled for OxPL/apoB and Lp(a) in both sexes (Tables 6-7). In pooled analyses, a 1-SD increase in OxPL/apoB was associated with a 37% (95% CI: 19% to 58%) increased risk of PAD, adjusting for all covariates. A 1-SD increase in Lp(a) was associated with almost the same magnitude of increased risk of PAD. With tertiles to categorize OxPL/apoB and Lp(a), men and women in the highest compared with lowest tertile of both biomarkers had approximately double the risk of PAD.

TABLE 6

Relative Risk and 95% CIs for Peripheral Artery Disease According to OxPL/ApoB Level

| | Women | | | | | | | | |
|---|---|---|---|---|---|---|---|---|---|
| | Per 1-SD Increase | Tertile | | | | Per 1-SD Increase | Tertile | | |
| | (7.17) | 1 | 2 | 3 | | (4.142) | 1 | 2 | 3 |
| Range (nM) | | 0.00-3.72 | 3.73-9.55 | 9.56-46.09 | Range (RLU) | | 0-2,150 | 2,151-5,517 | 5,518-26,622 |
| Cases | 144 | 33 | 43 | 68 | Cases | 144 | 33 | 43 | 68 |
| Model 1 | 1.53 (1.30-1.79) | 1.0 (ref) | 1.44 (0.86-2.41) | 2.73 (1.67-4.48) | Model 1 | 1.53 (1.30-1.79) | 1.0 (ref) | 1.44 (0.86-2.41) | 2.73 (1.67-4.48) |
| Model 2 | 1.50 (1.26-1.79) | 1.0 (ref) | 1.58 (0.91-2.75) | 2.92 (1.71-5.00) | Model 2 | 1.50 (1.26-1.79) | 1.0 (ref) | 1.58 (0.91-2.75) | 2.92 (1.71-5.00) |
| Model 3 | 1.51 (1.24-1.85) | 1.0 (ref) | 1.38 (0.75-2.54) | 2.55 (1.41-4.64) | Model 3 | 1.51 (1.24-1.85) | 1.0 (ref) | 1.38 (0.75-2.54) | 2.55 (1.41-4.64) |

| | Men | | | | | | | | |
|---|---|---|---|---|---|---|---|---|---|
| | Per 1-SD Increase | Tertile | | | | Per 1-SD Increase | Tertile | | |
| | (10.38) | 1 | 2 | 3 | | (5.999) | 1 | 2 | 3 |
| Range (nM) | | 7.85-12.93 | 12.94-16.85 | 16.86-82.75 | Range (RLU) | | 4.535-7.518 | 7,519-9,730 | 9,731-47,792 |
| Cases | 143 | 41 | 47 | 55 | Cases | 143 | 42 | 46 | 55 |
| Model 1 | 1.24 (1.05-1.46) | 1.0 (ref) | 1.15 (0.70-1.87) | 1.50 (0.92-2.46) | Model 1 | 1.24 (1.05-1.46) | 1.0 (ref) | 1.09 (0.67-1.78) | 1.46 (0.90-2.38) |
| Model 2 | 1.31 (1.09-1.58) | 1.0 (ref) | 1.23 (0.72-2.08) | 1.78 (1.03-3.09) | Model 2 | 1.31 (1.09-1.58) | 1.0 (ref) | 1.15 (0.68-1.96) | 1.72 (0.99-2.97) |
| Model 3 | 1.23 (1.00-1.52) | 1.0 (ref) | 1.03 (0.57-1.86) | 1.50 (0.81-2.78) | Model 3 | 1.23 (1.00-1.52) | 1.0 (ref) | 0.99 (0.55-1.79) | 1.46 (0.79-2.70) |

TABLE 6-continued

Relative Risk and 95% CIs for Peripheral Artery Disease According to OxPL/ApoB Level

| | | | Pooled | | | | | | |
|---|---|---|---|---|---|---|---|---|---|
| Model 3 | 1.37 (1.19-1.58) | 1.0 (ref) | 1.18 (0.77-1.82) | 1.97 (1.28-3.03) | Model 3 | 1.37 (1.18-1.58) | 1.0 (ref) | 1.17 (0.76-1.80) | 1.95 (1.27-3.00) |

Values are relative risk (95% CI) unless otherwise indicated.
Model 1: adjusted for matching factors (age, race [women only], month of blood draw, fasting status, and smoking).
Model 2: adjusted for matching factors, triglycerides, HDL-C, LDL-C, hsCRP, and HbA1c.
Model 3: adjusted for matching factors, triglycerides, HDL-C, LDL-C, hsCRP, HbA1c, parental history of MI before 60 years of age, pack-years of smoking, physical activity, hypertension, diabetes, hypercholesterolemia, BMI, aspirin use, and post-menopausal hormone use (women only).
CI = confidence interval; other abbreviations as in Table 5.

TABLE 7

Relative Risk and 95% CI for PAD based on Lp(a) Levels

| | Women | | | |
|---|---|---|---|---|
| | Per 1-SD Increase (28.8) | Tertile 1 | Tertile 2 | Tertile 3 |
| Range (mg/dl) | | 0.1-8.4 | 8.5-35.0 | 35.1-144.6 |
| Cases | 144 | 35 | 37 | 72 |
| Model 1 | 1.57 (1.33-1.86) | 1.0 (ref) | 1.04 (0.62-1.75) | 2.64 (1.64-4.26) |
| Model 2 | 1.54 (1.28-1.85) | 1.0 (ref) | 1.11 (0.64-1.94) | 2.76 (1.64-4.67) |
| Model 3 | 1.52 (1.24-1.87) | 1.0 (ref) | 1.37 (0.72-2.58) | 2.91 (1.58-5.36) |

| | Men | | | |
|---|---|---|---|---|
| | Per 1-SD Increase (22.8) | Tertile 1 | Tertile 2 | Tertile 3 |
| Range (mg/dl) | | 0.1-2.4 | 2.5-12.0 | 12.1-129.1 |
| Cases | 143 | 31 | 52 | 60 |
| Model 1 | 1.29 (1.09-1.52) | 1.0 (ref) | 1.88 (1.13-3.13) | 2.51 (1.49-4.21) |
| Model 2 | 1.27 (1.05-1.53) | 1.0 (ref) | 1.27 (0.73-2.22) | 1.91 (1.08-3.39) |
| Model 3 | 1.24 (1.00-1.53) | 1.0 (ref) | 1.20 (0.64-2.25) | 1.59 (0.84-3.00) |
| | Pooled | | | |
| Model 3 | 1.36 (1.18-1.57) | 1.0 (ref) | 1.28 (0.82-2.00) | 2.18 (1.40-3.39) |

Values are relative risk (95% CI) unless otherwise indicated.
Model 1: adjusted for matching factors (age, race [women only], month of blood draw, fasting status, and smoking).
Model 2: adjusted for matching factors, triglycerides, HDL-C, LDL-C, hsCRP, and HbA1c..
Model 3: adjusted for matching factors, triglycerides, HDL-C, LDL-C, hsCRP, HbA1c, parental history of MI before 60 years of age, pack-years of smoking, physical activity, hypertension, diabetes, hypercholesterolemia, BMI, aspirin use, and post-menopausal hormone use (women only).
Lp(a) = lipoprotein (a); other abbreviations as in Table 5.

IgG and IgM Autoantibodies and Immune Complexes.

No consistent associations of autoantibodies to MDA-LDL with risk of PAD were identified. The relative risks fluctuated across tertiles and the CIs were consistent with a broad range of risk estimates (Table 8), although it was of interest that there was a significant inverse relationship of IgG to MDA-LDL in men but not women. The IgG and IgM ApoB-IC were not statistically significantly associated with risk of PAD in men or in women, either as continuous variables or in tertiles (Table 9).

OxPL/apoB and Lp(a) in Context.

Figure 8:
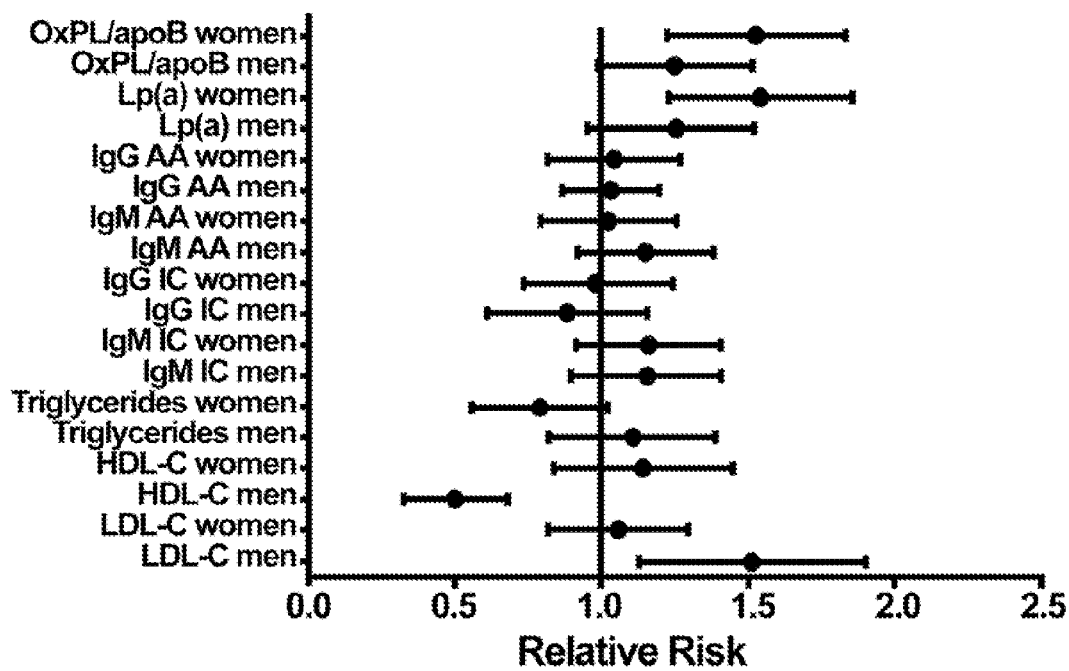
FIG. 8 shows adjusted relationship between oxidation-specific and standard biomarkers and RR of PAD.

In women, the C-statistic value for area under the receiver-operating characteristic curve increased from 0.725 to 0.756 and 0.761 with the addition of OxPL/apoB and Lp(a), respectively, to a list of traditional risk factors (Table 10). These risk factors include age, race (women only), month of blood draw, fasting status, smoking status, parental history of MI before age 60, pack-years of smoking, physical activity, hypertension, diabetes, hypercholesterolemia, BMI, aspirin use, and post-menopausal hormone use (women only). In men, the improvement was smaller: 0.728 to 0.731 and 0.735 with the addition of OxPL/apoB and Lp(a), respectively. Comparing OxPL/apoB and Lp(a) with other standard biomarkers, the magnitude of association between a 1-SD increase in OxPL/apoB and Lp(a) and risk of PAD was similar to that for LDL cholesterol and high-density lipoprotein cholesterol in men (FIG. 8).

TABLE 8

Relative Risk and 95% CIs for PAD based on MDA-LDL AutoAntibodies

| | IgG AA | | | | | IgM AA | | | |
|---|---|---|---|---|---|---|---|---|---|
| | Per 1-SD Increase log(IgG AA) | Tertile | | | | Per 1-SD Increase | Tertile | | |
| | | 1 | 2 | 3 | | | 1 | 2 | 3 |
| Women | | | | | | | | | |
| Range (RLU) | | 1,465-6,580 | 6,581-11,017 | 11,018-57,009 | Range (RLU) | | 2,013-15,741 | 15,742-22,494 | 22,495-77,968 |
| Cases | 144 | 40 | 56 | 48 | Cases | 144 | 50 | 34 | 60 |
| Model 1 | 1.16 (0.96-1.40) | 1.0 (ref) | 1.53 (0.95-2.45) | 1.26 (0.78-2.02) | Model 1 | 1.13 (0.95-1.36) | 1.0 (ref) | 0.59 (0.35-0.98) | 1.34 (0.84-2.13) |
| Model 2 | 1.16 (0.95-1.42) | 1.0 (ref) | 1.48 (0.89-2.46) | 1.32 (0.80-2.17) | Model 2 | 1.10 (0.91-1.34) | 1.0 (ref) | 0.57 (0.34-0.97) | 1.32 (0.81-2.17) |
| Model 3 | 1.10 (0.88-1.37) | 1.0 (ref) | 1.42 (0.79-2.53) | 1.13 (0.65-1.96) | Model 3 | 1.00 (0.80-1.26) | 1.0 (ref) | 0.47 (0.26-0.85) | 1.05 (0.60-1.85) |
| Men | | | | | | | | | |
| Range (RLU) | | 485-1,940 | 1,941-3,690 | 3,691-64,956 | Range (RLU) | | 732-7,203 | 7,204-11,833 | 11,834-94,623 |
| Cases | 143 | 57 | 40 | 46 | Cases | 143 | 45 | 44 | 54 |
| Model 1 | 0.94 (0.79-1.12) | 1.0 (ref) | 0.57 (0.35-0.93) | 0.73 (0.46-1.15) | Model 1 | 1.13 (0.96-1.34) | 1.0 (ref) | 0.91 (0.56-1.49) | 1.25 (0.80-1.97) |
| Model 2 | 0.87 (0.71-1.06) | 1.0 (ref) | 0.52 (0.30-0.89) | 0.54 (0.32-0.92) | Model 2 | 1.18 (0.97-1.43) | 1.0 (ref) | 0.83 (0.48-1.43) | 1.17 (0.70-1.96) |
| Model 3 | 0.84 (0.67-1.06) | 1.0 (ref) | 0.58 (0.31-1.08) | 0.52 (0.29-0.95) | Model 3 | 1.13 (0.93-1.39) | 1.0 (ref) | 1.02 (0.55-1.87) | 1.26 (0.71-2.23) |

Values are relative risk (95% CI) unless otherwise indicated.
Model 1: adjusted for matching factors (age, race [women only], month of blood draw, fasting status, and smoking status).
Model 2: adjusted for matching factors, triglycerides, HDL-C, LDL-C, hsCRP, and HbA$_{1c}$.
Model 3: adjusted for matching factors, triglycerides, HDL-C, LDL-C, hsCRP, HbA$_{1c}$, parental history of MI before 60 years of age, pack-years of smoking, physical activity, hypertension, diabetes, hypercholesterolemia, BMI, aspirin use, and post-menopausal hormone use (women only).

TABLE 9

Relative Risk and 95% CIs for PAD based on Level of IC

| | IgG ApoB-IC | | | | | IgM ApoB-IC | | | |
|---|---|---|---|---|---|---|---|---|---|
| | Per 1-SD Increase | Tertile | | | | Per 1-SD Increase | Tertile | | |
| | | 1 | 2 | 3 | | | 1 | 2 | 3 |
| Women | | | | | | | | | |
| Range (RLU) | | 272-906 | 907-1,328 | 1,329-12,372 | Range (RLU) | | 23-1,442 | 1,143-2,050 | 2,051-21,500 |
| Cases | 144 | 41 | 58 | 45 | Cases | 144 | 49 | 52 | 53 |
| Model 1 | 1.00 (0.82-1.21) | 1.0 (ref) | 1.53 (0.96-2.44) | 1.15 (0.71-1.88) | Model 1 | 1.13 (0.95-1.33) | 1.0 (ref) | 0.78 (0.48-1.26) | 1.13 (0.71-1.80) |
| Model 2 | 0.97 (0.78-1.20) | 1.0 (ref) | 1.55 (0.94-2.55) | 1.08 (0.64-1.83) | Model 2 | 1.15 (0.96-1.38) | 1.0 (ref) | 0.82 (0.49-1.38) | 1.21 (0.74-1.98) |
| Model 3 | 0.96 (0.73-1.24) | 1.0 (ref) | 1.67 (0.96-2.93) | 0.94 (0.51-1.74) | Model 3 | 1.14 (0.92-1.41) | 1.0 (ref) | 0.78 (0.45-1.37) | 1.08 (0.61-1.91) |
| Men | | | | | | | | | |
| Range (RLU) | | 459-1,460 | 1,461-2,061 | 2,062-28,725 | Range (RLU) | | 96-685 | 686-1,235 | 1,236-59,411 |
| Cases | 143 | 54 | 43 | 46 | Cases | 143 | 49 | 47 | 47 |
| Model 1 | 0.88 (0.68-1.13) | 1.0 (ref) | 0.68 (0.43-1.08) | 0.77 (0.48-1.24) | Model 1 | 1.08 (0.97-1.21) | 1.0 (ref) | 0.90 (0.57-1.43) | 0.94 (0.60-1.48) |
| Model 2 | 0.89 (0.68-1.15) | 1.0 (ref) | 0.65 (0.38-1.09) | 0.84 (0.49-1.44) | Model 2 | 1.10 (0.93-1.31) | 1.0 (ref) | 0.90 (0.54-1.52) | 0.97 (0.59-1.59) |
| Model 3 | 0.86 (0.63-1.17) | 1.0 (ref) | 0.65 (0.36-1.19) | 0.98 (0.53-1.82) | Model 3 | 1.13 (0.91-1.42) | 1.0 (ref) | 1.11 (0.63-1.97) | 0.97 (0.55-1.73) |

Values are n (range) unless otherwise indicated.
Model 1: adjusted for matching factors (age, race [women only], month of blood draw, fasting status, and smoking status).
Model 2: adjusted for matching factors, triglycerides, HDL-C, LDL-C, hsCRP, and HbA$_{1c}$.
Model 3: adjusted for matching factors, triglycerides, HDL-C, LDL-C, hsCRP, HbA$_{1c}$, parental history of MI before age 60, pack-years of smoking, physical activity, hypertension, diabetes, hypercholesterolemia, BMI, aspirin use and post-menopausal hormone use (women only).

TABLE 10

C-Statistic Values for Area Under the Receiver-Operating Characteristic Curves

| | Women | Men |
|---|---|---|
| Traditional risk factors | 0.725 | 0.728 |
| Traditional risk factors + OxPL/apoB | 0.756 | 0.731 |
| Traditional risk factors + Lp(a) | 0.761 | 0.735 |
| Traditional risk factors + triglycerides | 0.727 | 0.741 |
| Traditional risk factors + HDL-C | 0.726 | 0.761 |
| Traditional risk factors + LDL-C | 0.727 | 0.734 |
| Traditional risk factors, OxPL/apoB, Lp(a) | 0.759 | 0.736 |
| Traditional risk factors, OxPL/apoB, Lp(a), triglycerides | 0.762 | 0.749 |
| Traditional risk factors, OxPL/apoB, Lp(a), triglycerides, HDL-C | 0.763 | 0.769 |
| Traditional risk factors, OxPL/apoB, Lp(a), triglycerides, HDL-C, LDL-C | 0.763 | 0.780 |

Traditional risk factors: matching factors (age, race [woman only], month of of blood draw, fasting status, and smoking status), parental history of MI before 60 years of age, pack-years of smoking, physical activity, hypertension, diabetes, hypercholesterolemia, BMI, aspirin use, and post-menopausal hormone use (women only).

A number of embodiments of the invention have been described. Nevertheless, it will be understood that various modifications may be made without departing from the spirit and scope of the invention. Accordingly, other embodiments are within the scope of the following claims.

---

What is claimed is:

1. A method for determine a risk of stroke, a transient ischemic attack (TIA) or peripheral artery disease (PAD) in a subject, the method comprising:
   a) obtaining a sample comprising plasma from a subject;
   b) determining the level of oxidized phospholipid (OxPL) on apolipoprotein B-100 (apoB) (OxPL/apoB) in the sample by contacting the OxPL and apoB with antibodies that specifically bind to the OxPL or apoB;
   c) determining the level of IgG and/or IgM autoantibodies to oxidation-specific epitopes (OSEs) comprising contacting the sample with a peptide mimotope selected from the group consisting of: NNWNMPL (SEQ ID NO:24); NNRNMPL (SEQ ID NO:25); NNYNMPL (SEQ ID NO:26); NNQNMPL (SEQ ID NO:27); NNWKMPL (SEQ ID NO:28); NNSHMPL (SEQ ID NO:29); KNSXQPL (SEQ ID NO:30); NNSXMPL (SEQ ID NO:31); QNSHMPL (SEQ ID NO:32); NNSNMPL (SEQ ID NO:35); NNSKMRL (SEQ ID NO:33); and DWAPHFT (SEQ ID NO:34), wherein the IgG and/or IgM autoantibodies bind to the peptide mimotope; and
   d) comparing the levels of IgG and/or IgM autoantibodies to OSEs in the sample to values of IgG and/or IgM autoantibodies indicative of high risk of stroke, TIA and/or PAD, and comparing the level of OxPL/apoB obtained from the sample with levels indicative of high risk of stroke, TIA and/or PAD, wherein if the level of OxPL/apoB and IgG and/or IgM autoantibodies in the sample falls within the levels OxPL/apoB and IgG and/or IgM autoantibodies of subject with high risk of stroke, TIA and/or PAD, the level in the sample of the subject is predictive for the risk of stroke, TIA and/or PAD in the subject.

2. The method of claim 1, wherein the peptide mimotope further comprises from 1-10 additional amino acids at either then N-terminal or C-terminal ends.

3. The method of claim 1, wherein the IgG and/or IdM autoantibodies bind malondialdehyde (MDA)-OxPL.

4. The method of claim 1, wherein the IgG and/or IgM autoantibodies bind to a OxPL selected from the group consisting of 1-palmitoyl-2-arachidonoyl-sn-glycero-3phosphorylcholine (Ox-PAPC), 1-palmitoyl-2-oxovaleroyl-sn-glycero-3-phosphoryl-choline (POVPC), 1-palmitoyl-glutaroyl-sn-glycero-3-phosphorylcholine (PGPC), 1-palmitoyl-2-epoxyisoprostane-sn-glycero-3-phosphorylcholine (Ox-SAPC), 1-stearoyl-2-oxovaleroyl-sn-glycero-3-phosphorylcholine (SOVPC), 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine (Ox-SAPE), 1-stearoyl-2-oxovaleroyl-sn-glycero-3-phosphorylethanolamine (SOVPE), 1-stearoyl-2-glutaroyl-sn-glycero-3-phosphorylethanolamine (SGPE), and 1-stearoyl-2-epoxyisoprostane-sn-glycero-3-phosphorylethanolamine (SEIPE).

5. The method of claim 1, wherein the level of OxPL and the level of total apoB in the sample are measured with two or more different antibodies, wherein a first antibody specifically interacts with OxPL and a second antibody specifically interacts with apoB.

6. The method of claim 5, wherein the antibodies are monoclonal antibodies.

7. The method of claim 6, wherein the antibody that interacts with OxPL is E06, DLH3 or any antibody binding a OxPL epitope.

8. The method of claim 1, wherein the method further comprises correlating the level of OxPL/apoB and IgG and/or IgM for the subject with:
   a) the age of the subject at the time the sample is obtained;
   b) the subject's gender; and/or
   c) the subject's race.

9. The method of claim 1 further comprising correlating the value or ratio for the subject with other risk factors selected from the group consisting of current smoking, hypertension, LDL cholesterol levels, and triglyceride levels.

10. The method of claim 1, further comprising determining the level of Lp(a) lipoprotein from the sample and comparing the Lp(a) lipoprotein level for the subject with Lp(a) lipoprotein levels from subjects at high risk or with documented coronary artery disease (CAD), acute coronary syndrome (ACS), or at risk for ACS, wherein if the Lp(a) lipoprotein level for the subject falls within the Lp(a) lipoprotein level range from subjects at high risk or with documented CAD, ACS, or at risk for ACS, is predictive for the risk of stroke or TIA in the subject.

11. The method of claim 1, wherein if the IgG levels fall within the upper tertile of values from a general population, then the subject is at risk for coronary vascular disease (CVD), TIA or stroke.

12. The method of claim 1, wherein if the IgM levels fall within the lower tertile of values from a general population, then the subject is at risk for coronary vascular disease (CVD), TIA or stroke.

13. The method of claim 1, wherein the samples are obtained at two different time points.

14. The method of claim 13, wherein the IgM and/or IgG levels are compared between a current and prior measurement of IgM and/or IgG levels, wherein an increase in IgM levels is indicative of a reduced risk of coronary vascular disease (CVD), stroke or TIA.

15. The method of claim 1, wherein if the OxPL/apoB value falls within the lowest quartile, the subject has a low risk of stroke, TIA or PAD.

16. The method of claim 1, wherein if the OxPL/apoB value falls above the lowest quartile for a standard population, then the subject is at-risk for a stroke, TIA or PAD.

* * * * *

SEQUENCE LISTING

```
<160> NUMBER OF SEQ ID NOS: 35

<210> SEQ ID NO 1
<211> LENGTH: 12
<212> TYPE: PRT
<213> ORGANISM: Artificial Sequence
<220> FEATURE:
<223> OTHER INFORMATION: Consensus mimotope sequence
<220> FEATURE:
<221> NAME/KEY: MISC_FEATURE
<222> LOCATION: (1)..(1)
<223> OTHER INFORMATION: Xaa is N, E, Q, A, H, T, G or D
<220> FEATURE:
<221> NAME/KEY: MISC_FEATURE
<222> LOCATION: (2)..(2)
<223> OTHER INFORMATION: Xaa is S, N, V, R, A, W, Y or D
<220> FEATURE:
<221> NAME/KEY: MISC_FEATURE
<222> LOCATION: (3)..(3)
<223> OTHER INFORMATION: Xaa is W, R, Y, M, I, L, V, G, T or P
<220> FEATURE:
<221> NAME/KEY: MISC_FEATURE
<222> LOCATION: (4)..(4)
<223> OTHER INFORMATION: Xaa is T, N, S or F
<220> FEATURE:
<221> NAME/KEY: MISC_FEATURE
<222> LOCATION: (5)..(5)
<223> OTHER INFORMATION: Xaa is N, K or S
<220> FEATURE:
<221> NAME/KEY: MISC_FEATURE
<222> LOCATION: (6)..(6)
<223> OTHER INFORMATION: Xaa is A, N, S, D, W, L, Y, T, I, V, K or P
<220> FEATURE:
<221> NAME/KEY: MISC_FEATURE
<222> LOCATION: (7)..(7)
<223> OTHER INFORMATION: Xaa is S, W, D, T, A, Q, M, E or P
<220> FEATURE:
<221> NAME/KEY: MISC_FEATURE
<222> LOCATION: (8)..(8)
<223> OTHER INFORMATION: Xaa is L, Q, A, V, G, M, H, S, E or N
<220> FEATURE:
<221> NAME/KEY: MISC_FEATURE
<222> LOCATION: (9)..(9)
<223> OTHER INFORMATION: Xaa is S, W, H, M, L, A, E, T, D, Q, or R
<220> FEATURE:
<221> NAME/KEY: MISC_FEATURE
<222> LOCATION: (10)..(10)
<223> OTHER INFORMATION: Xaa is T, Y, R, S, Q, L, F, V, A, D or I
<220> FEATURE:
<221> NAME/KEY: MISC_FEATURE
<222> LOCATION: (11)..(11)
<223> OTHER INFORMATION: Xaa is F, I, H, L, M, V, or P
<220> FEATURE:
<221> NAME/KEY: MISC_FEATURE
<222> LOCATION: (12)..(12)
<223> OTHER INFORMATION: Xaa is H, Q, G, S, M, A, P, W or L
```

```
<400> SEQUENCE: 1

Xaa Xaa Xaa Xaa Xaa Xaa Xaa Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Consensus cyclic mimotope sequence
<220> FEATURE:
<221> NAME/KEY: MISC_FEATURE
<222> LOCATION: (1)..(1)
<223> OTHER INFORMATION: Xaa is N, K, Q or D
<220> FEATURE:
<221> NAME/KEY: MISC_FEATURE
<222> LOCATION: (2)..(2)
<223> OTHER INFORMATION: Xaa is N or W
<220> FEATURE:
<221> NAME/KEY: MISC_FEATURE
<222> LOCATION: (3)..(3)
<223> OTHER INFORMATION: Xaa is W, R, Y, Q, S or A
<220> FEATURE:
<221> NAME/KEY: MISC_FEATURE
<222> LOCATION: (4)..(4)
<223> OTHER INFORMATION: Xaa is N, K, H or P
<220> FEATURE:
<221> NAME/KEY: MISC_FEATURE
<222> LOCATION: (5)..(5)
<223> OTHER INFORMATION: Xaa is M, Q or H
<220> FEATURE:
<221> NAME/KEY: MISC_FEATURE
<222> LOCATION: (6)..(6)
<223> OTHER INFORMATION: Xaa is P, R or F
<220> FEATURE:
<221> NAME/KEY: MISC_FEATURE
<222> LOCATION: (7)..(7)
<223> OTHER INFORMATION: Xaa is L or T

<400> SEQUENCE: 2

Xaa Xaa Xaa Xaa Xaa Xaa Xaa
1               5

<210> SEQ ID NO 3
<211> LENGTH: 12
<212> TYPE: PRT
<213> ORGANISM: Artificial Sequence
<220> FEATURE:
<223> OTHER INFORMATION: Peptide mimotope

<400> SEQUENCE: 3

Asn Ser Trp Thr Asn Ala Ser Leu Ser Thr Phe His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Peptide mimotope

<400> SEQUENCE: 4

Asn Ser Arg Thr Asn Asn Ser Gln Trp Thr Phe Gln
1               5                   10

<210> SEQ ID NO 5
<211> LENGTH: 12
<212> TYPE: PRT
<213> ORGANISM: Artificial Sequence
<220> FEATURE:
```

```
<223> OTHER INFORMATION: Peptide mimotope

<400> SEQUENCE: 5

Glu Ser Trp Thr Asn Ser Trp Ala His Tyr Phe Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Peptide mimotope

<400> SEQUENCE: 6

Glu Ser Trp Thr Asn Ser Trp Ala Met Tyr Phe Gly
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Peptide mimotope

<400> SEQUENCE: 7

Gln Ser Tyr Thr Asn Asp Asp Val Leu Arg Ile Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Peptide mimotope

<400> SEQUENCE: 8

Gln Asn Met Asn Asn Trp Thr Leu Ala Ser Ile Met
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Peptide mimotope

<400> SEQUENCE: 9

Glu Val Met Asn Asn Trp Thr Leu Ala Ser Ile Met
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Peptide mimotope

<400> SEQUENCE: 10

Ala Ser Ile Ser Asn Leu Thr Leu Ser Arg Phe Met
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Peptide mimotope
```

```
<400> SEQUENCE: 11

His Ser Trp Ser Asn Tyr Trp Gly His Gln His Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Peptide mimotope

<400> SEQUENCE: 12

His Arg Ile Ser Asn Tyr Ala Met Glu Leu His Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Peptide mimotope

<400> SEQUENCE: 13

His Ser Leu Thr Asn Thr Gln Met Thr Gln Leu Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Peptide mimotope

<400> SEQUENCE: 14

His Ser Leu Ser Asn Ile Gln Met Ala Thr Leu Ala
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Peptide mimotope

<400> SEQUENCE: 15

His Arg Met Thr Asn Ala Met His His Phe Met Gly
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Peptide mimotope

<400> SEQUENCE: 16

His Arg Met Thr Asn Asn Ala Met Asp Val Phe Met
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Peptide mimotope
```

```
<400> SEQUENCE: 17

His Arg Leu Thr Asn Ser Glu Gln Ala Ala Leu Pro
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Peptide mimotope

<400> SEQUENCE: 18

Thr Ala Val Thr Asn Ser Met Met Glu Arg Leu Trp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Peptide mimotope

<400> SEQUENCE: 19

Gly Trp Gly Asn Lys Thr Pro Ser Gln Asp Val His
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Peptide mimotope

<400> SEQUENCE: 20

Asp Tyr Thr Asn Ser Val Ser Met Arg Tyr Leu Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Peptide mimotope

<400> SEQUENCE: 21

His Gln Leu Ser Asn Lys Asp Glu Gln Thr Pro Gln
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Peptide mimotope

<400> SEQUENCE: 22

Ala Asp Pro Phe Ser Pro Thr Asn Arg Ile Pro Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: P1 mimotope

<400> SEQUENCE: 23
```

```
His Ser Trp Thr Asn Ser Trp Met Ala Thr Phe Leu
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Peptide mimotope

<400> SEQUENCE: 24

Asn Asn Trp Asn Met Pro Leu
1               5

<210> SEQ ID NO 25
<211> LENGTH: 7
<212> TYPE: PRT
<213> ORGANISM: Artificial Sequence
<220> FEATURE:
<223> OTHER INFORMATION: Peptide mimotope

<400> SEQUENCE: 25

Asn Asn Arg Asn Met Pro Leu
1               5

<210> SEQ ID NO 26
<211> LENGTH: 7
<212> TYPE: PRT
<213> ORGANISM: Artificial Sequence
<220> FEATURE:
<223> OTHER INFORMATION: Peptide mimotope

<400> SEQUENCE: 26

Asn Asn Tyr Asn Met Pro Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Peptide mimotope

<400> SEQUENCE: 27

Asn Asn Gln Asn Met Pro Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Peptide mimotope

<400> SEQUENCE: 28

Asn Asn Trp Lys Met Pro Leu
1               5

<210> SEQ ID NO 29
<211> LENGTH: 7
<212> TYPE: PRT
<213> ORGANISM: Artificial Sequence
<220> FEATURE:
<223> OTHER INFORMATION: Peptide mimotope

<400> SEQUENCE: 29
```

```
Asn Asn Ser His Met Pro Leu
1               5

<210> SEQ ID NO 30
<211> LENGTH: 7
<212> TYPE: PRT
<213> ORGANISM: Artificial Sequence
<220> FEATURE:
<223> OTHER INFORMATION: Peptide mimotope
<220> FEATURE:
<221> NAME/KEY: misc_feature
<222> LOCATION: (4)..(4)
<223> OTHER INFORMATION: Xaa can be any naturally occurring amino acid

<400> SEQUENCE: 30

Lys Asn Ser Xaa Gln Pro Leu
1               5

<210> SEQ ID NO 31
<211> LENGTH: 7
<212> TYPE: PRT
<213> ORGANISM: Artificial Sequence
<220> FEATURE:
<223> OTHER INFORMATION: Peptide mimotope
<220> FEATURE:
<221> NAME/KEY: misc_feature
<222> LOCATION: (4)..(4)
<223> OTHER INFORMATION: Xaa can be any naturally occurring amino acid

<400> SEQUENCE: 31

Asn Asn Ser Xaa Met Pro Leu
1               5

<210> SEQ ID NO 32
<211> LENGTH: 7
<212> TYPE: PRT
<213> ORGANISM: Artificial Sequence
<220> FEATURE:
<223> OTHER INFORMATION: Peptide mimotope

<400> SEQUENCE: 32

Gln Asn Ser His Met Pro Leu
1               5

<210> SEQ ID NO 33
<211> LENGTH: 7
<212> TYPE: PRT
<213> ORGANISM: Artificial Sequence
<220> FEATURE:
<223> OTHER INFORMATION: Peptide mimotope

<400> SEQUENCE: 33

Asn Asn Ser Lys Met Arg Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Peptide mimotope

<400> SEQUENCE: 34

Asp Trp Ala Pro His Phe Thr
1               5

<210> SEQ ID NO 35
<211> LENGTH: 7
```

```
<212> TYPE: PRT
<213> ORGANISM: Artificial Sequence
<220> FEATURE:
<223> OTHER INFORMATION: P2 mimotope

<400> SEQUENCE: 35

Asn Asn Ser Asn Met Pro Leu
1               5
```